United States Patent
Heidelbaugh et al.

(10) Patent No.: US 8,362,022 B2
(45) Date of Patent: Jan. 29, 2013

(54) SELECTIVE SUBTYPE ALPHA 2 ADRENERGIC AGENTS AND METHODS FOR USE THEREOF

(75) Inventors: Todd M. Heidelbaugh, Fountain Valley, CA (US); Ken Chow, Newport Coast, CA (US); Santosh C. Sinha, Ladera Ranch, CA (US); Phong X. Nguyen, Placentia, CA (US); Wenkui K. Fang, Irvine, CA (US); Ling Li, Irvine, CA (US); Janet A. Takeuchi, Anaheim, CA (US); Smita S. Bhat, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 239 days.

(21) Appl. No.: 12/811,773

(22) PCT Filed: Jan. 14, 2009

(86) PCT No.: PCT/US2009/030886
§ 371 (c)(1),
(2), (4) Date: Oct. 26, 2010

(87) PCT Pub. No.: WO2009/091759
PCT Pub. Date: Jul. 23, 2009

(65) Prior Publication Data
US 2011/0034517 A1 Feb. 10, 2011

Related U.S. Application Data

(60) Provisional application No. 61/022,158, filed on Jan. 18, 2008.

(51) Int. Cl.
*A61K 31/497* (2006.01)
*A61K 31/4439* (2006.01)
(52) U.S. Cl. .................. 514/255.05; 514/341; 544/336; 546/274.7
(58) Field of Classification Search .................. 544/336; 546/274.7
See application file for complete search history.

(56) References Cited

FOREIGN PATENT DOCUMENTS
WO  WO 92/00073  1/1992
WO  WO 2005/063724  7/2005

OTHER PUBLICATIONS

Robert R. Ruffolo, Jr., alpha-Adrenoreceptors: Molecular Biology, Biochemistry and Pharmacology, (Progress in Basic and Clinical Pharmacology series, Karger, 1991).
Kim and Chung 1992, Pain 150, pp. 355-363.
Messier et. al., 1995, Pharmacol. Toxicol. 76, pp. 308-311.
Conklin et al. (1993) Nature 363:274-6, Receptor Selection and Amplification Technology (RSAT).
Dixon, W.J., Ann. Rev. Pharmacol. Toxicol. 20:441-462 (1980).

*Primary Examiner* — Brian McDowell
(74) *Attorney, Agent, or Firm* — Doina G. Ene; John E. Wurst; Allergan, Inc.

(57) ABSTRACT

The invention provides well-defined heterocyclic compounds that are useful as subtype selective alpha 2 adrenergic agonists. As such, the compounds described herein, having the structure:

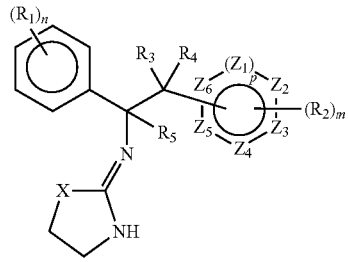

are useful in treating a wide variety of disorders associated with selective subtype modulation of alpha 2 adrenergic receptors.

6 Claims, 1 Drawing Sheet

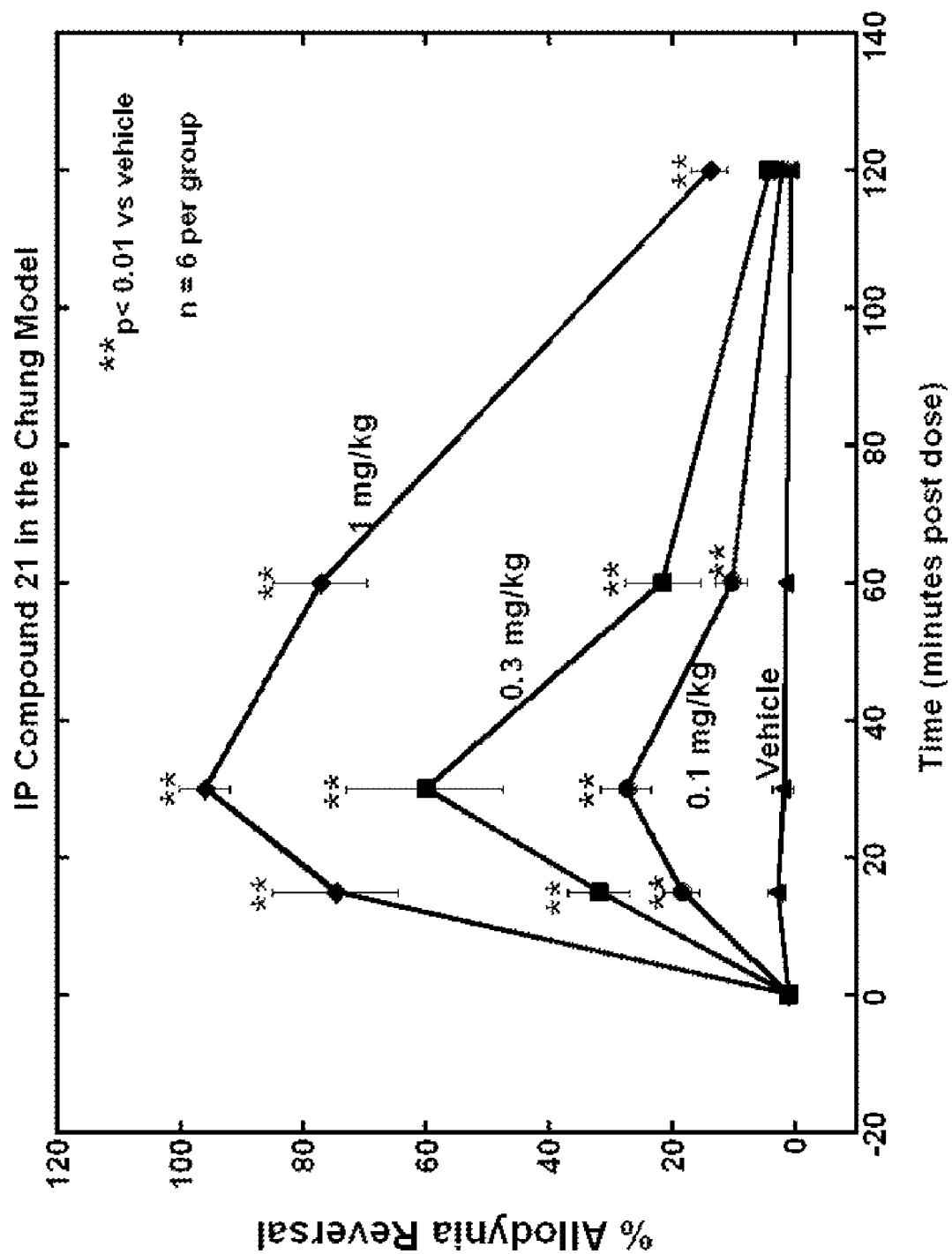

SELECTIVE SUBTYPE ALPHA 2 ADRENERGIC AGENTS AND METHODS FOR USE THEREOF

CROSS-REFERENCE

This application claims the benefit of U.S. Provisional Application Ser. No. 61/022,158, filed Jan. 18, 2008, which is hereby incorporated by reference in its entirety.

FIELD OF THE INVENTION

The present invention relates generally to certain heterocyclic compounds and to their use as agonists, for example as selective subtype agonists of alpha 2 adrenergic receptors. The invention relates specifically to the use of these compounds and pharmaceutical compositions to treat disorders associated with selective subtype alpha 2 adrenergic receptor modulation.

BACKGROUND OF THE INVENTION

Human adrenergic receptors are integral membrane proteins that have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, beta 1, and beta 2 subtypes. Functional differences between alpha 1 and alpha 2 receptors have been recognized, and compounds that exhibit selective binding between these two subtypes have been developed. Thus, in published international patent application WO 92/0073, the selective ability of the R(+) enantiomer of terazosin to selectively bind to adrenergic receptors of the alpha 1 subtype was reported. The alpha 1/alpha 2 selectivity of this compound was disclosed as being significant because agonist stimulation of the alpha 2 receptors was said to inhibit secretion of epinephrine and norepinephrine, while antagonism of the alpha 2 receptor was said to increase secretion of these hormones. Thus, the use of non-selective alpha-adrenergic blockers, such as phenoxybenzamine and phentolamine, was said to be limited by their alpha 2 adrenergic receptor mediated induction of increased plasma catecholamine concentration and the attendant physiological sequelae (increased heart rate and smooth muscle contraction).

For a further general background on the alpha-adrenergic receptors, the reader's attention is directed to Robert R. Ruffolo, Jr., alpha-Adrenoreceptors: Molecular Biology, Biochemistry and Pharmacology, (Progress in Basic and Clinical Pharmacology series, Karger, 1991), wherein the basis of alpha 1/alpha 2 subclassification, the molecular biology, signal transduction, agonist structure-activity relationships, receptor functions, and therapeutic applications for compounds exhibiting alpha-adrenergic receptor affinity is explored.

The cloning, sequencing and expression of alpha receptor subtypes from animal tissues has led to the subclassification of the alpha 1 adrenoreceptors into alpha 1A, alpha 1B and alpha 1D. Similarly, the alpha 2 adrenoreceptors have also been classified alpha 2A, alpha 2B, and alpha 2C receptors. Each alpha 2 receptor subtype appears to exhibit its own pharmacological and tissue specificities. Compounds having a degree of specificity for one or more of these subtypes may be more specific therapeutic agents for a given indication than an alpha 2 receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha 2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

SUMMARY OF THE INVENTION

The invention provides well-defined heterocyclic compounds that are useful as subtype selective alpha 2 adrenergic agonists. As such, the compounds described herein are useful in treating a wide variety of disorders associated with selective subtype modulation of alpha 2 adrenergic receptors.

In one embodiment of the invention, there are provided compounds having the structure:

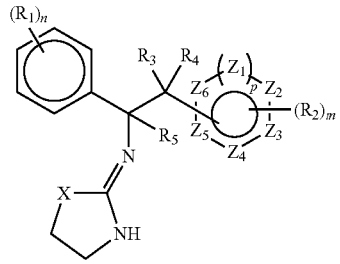

Structure 1 wherein:
X is O, S, or NH;
$Z_1$-$Z_6$ are each independently C, N, O, or S, with the proviso that at least one of $Z_1$-$Z_6$ is N;
n and m are each independently 1 to 5;
p is 0 or 1;
each $R_1$ and $R_2$ is independently H, lower alkyl, lower alkenyl, lower alkynyl, halide, hydroxy, alkoxy, trifluoromethyl, —N($R_6$)$_2$, —CN, —CO$_2$$R_6$, or —CH$_2$OH; or
when n is 2, each $R_1$ taken together with the carbon atoms to which they are attached forms a fused aryl, substituted aryl, heteroaryl, substituted heteroaryl, cycloalkyl, substituted cycloalkyl, heterocyclic, or substituted heterocyclic ring;

$R_3$, $R_4$, $R_5$, and $R_6$ are each independently H or lower alkyl;

or pharmaceutically acceptable salts thereof.

In another embodiment, there are provided pharmaceutical compositions including at least one compound of Structure 1 in a pharmaceutically acceptable carrier therefor.

In a further embodiment of the invention, there are provided methods for treating disorders associated with selective subtype modulation of alpha 2 adrenergic receptors. Such methods can be performed, for example, by administering to a subject in need thereof a pharmaceutical composition containing a therapeutically effective amount of a at least one compound of Structure 1.

In still another embodiment of the invention, there are provided methods for treating disorders associated with selective subtype modulation of alpha 2 adrenergic receptors, including administering to a subject in need thereof a therapeutically effective amount of at least one compound of Structure 1 or any combination thereof, or pharmaceutically acceptable salts, hydrates, solvates, crystal forms, isomers, tautomers, enantiomers, and diastereomers thereof.

BRIEF DESCRIPTION OF THE FIGURES

FIG. 1 demonstrates the ability of compounds of the invention to alleviate chronic pain. The data set forth in FIG. 1 were measured according to the Chung model (Kim and Chung 1992, Pain 150, pp 355-363).

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —CH$_2$OR$_7$, —C(O)—, —C(O)—, —S—, —S(O)$_2$, —OC(O)—O—, wherein $R_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

In addition, the heterocyclic compounds represented by Structure 1 can undergo tautomeric transformations and can be depicted by the tautomeric structures shown below. Referring to Structure 1, when X is N, the following exemplary tautomers are possible:

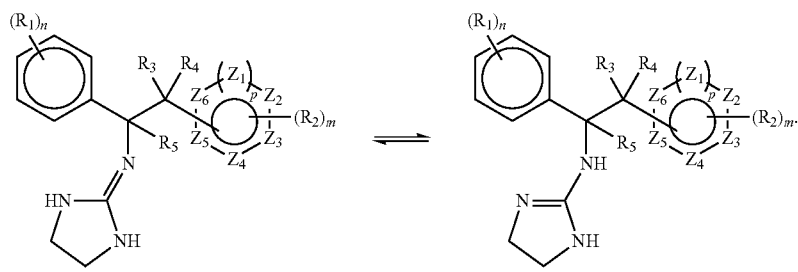

When X is S, the following exemplary tautomers are possible:

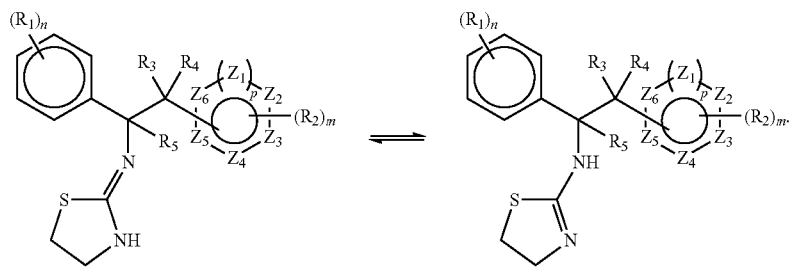

When X is O, the following exemplary tautomers are possible:

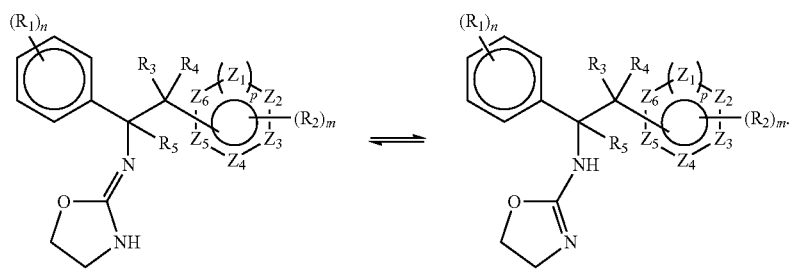

All tautomers of Structure 1 are within the scope of the invention.

The invention provides compounds having the structure:

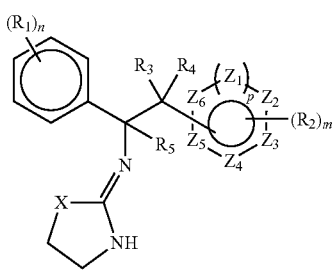

Structure 1 wherein:
X is O, S, or NH;
$Z_1$-$Z_6$ are each independently C, N, O, or S, with the proviso that at least one of $Z_1$-$Z_6$ is N;
n and m are each independently 1 to 5;
p is 0 or 1;

each $R_1$ and $R_2$ is independently H, lower alkyl, lower alkenyl, lower alkynyl, halide, hydroxy, alkoxy, trifluoromethyl, —N($R_6$)$_2$, —CN, —CO$_2$$R_6$, or —CH$_2$OH; or when n is 2, each $R_1$ taken together with the carbon atoms to which they are attached forms a fused aryl, substituted aryl, heteroaryl, substituted heteroaryl, cycloalkyl, substituted cycloalkyl, heterocyclic, or substituted heterocyclic ring;

$R_3$, $R_4$, $R_5$, and $R_6$ are each independently H or lower alkyl;

or pharmaceutically acceptable salts thereof.

In some embodiments, there are provided invention compounds according to Structure 1 wherein p is 1. In some embodiments, there are provided invention compounds according to Structure 1 wherein $R_1$ is H, lower alkyl, chloro, fluoro, trifluoromethyl, or methoxy.

In other embodiments of the invention, there are provided compounds having the structure Structure 2

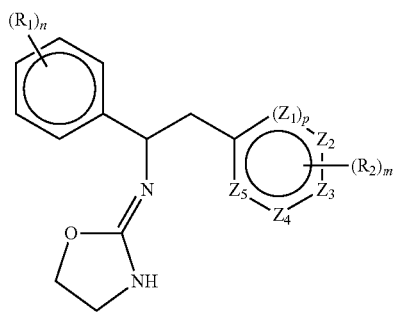

wherein:
$Z_1$-$Z_5$ are each independently C, N, O, or S, with the proviso that at least one of $Z_1$-$Z_5$ is N;
n and m are each independently 1 to 5;
p is 0 or 1;
each $R_1$ and $R_2$ is independently H, lower alkyl, halide, hydroxy, alkoxy, or trifluoromethyl;
or pharmaceutically acceptable salts thereof.

Exemplary compounds according to Structure 2 include, but are not limited to, the following structures:

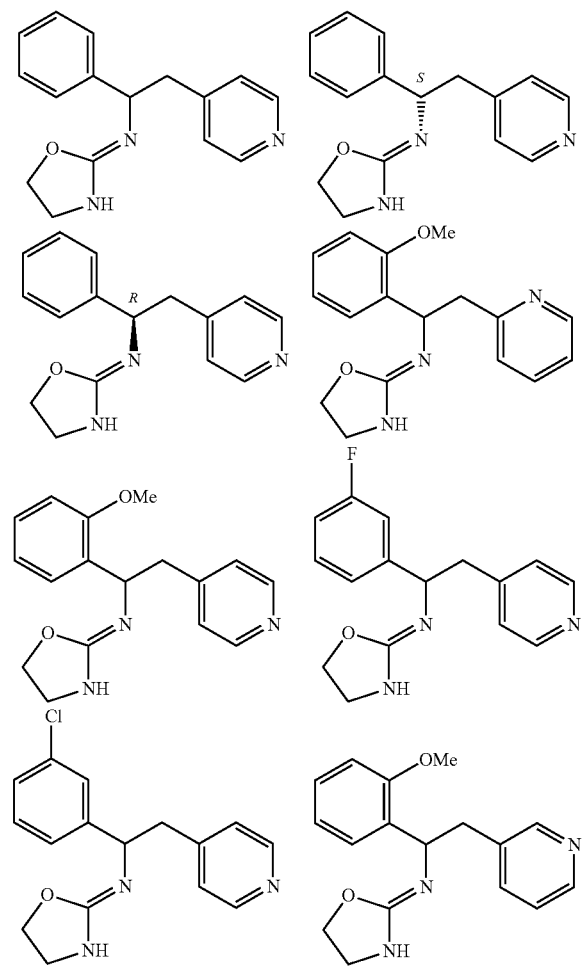

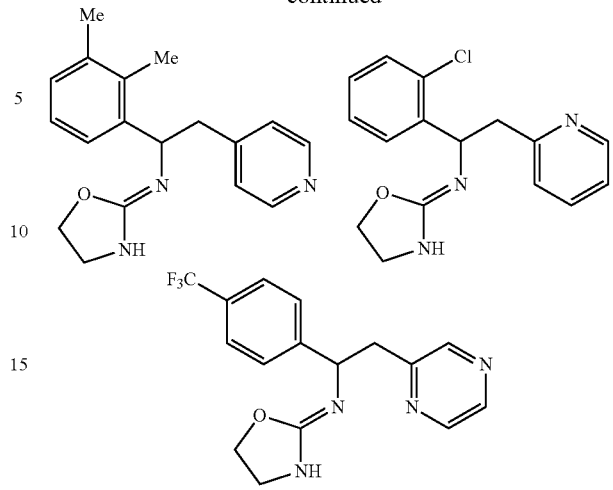

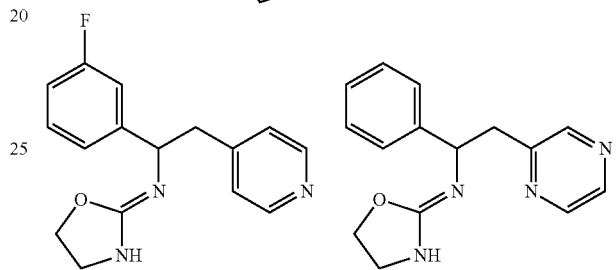

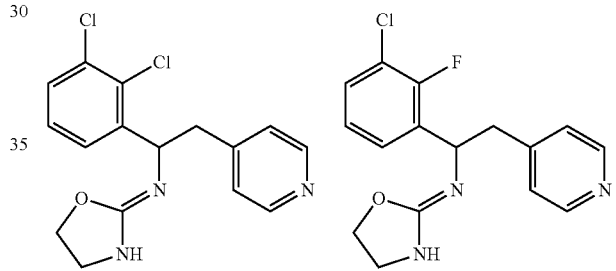

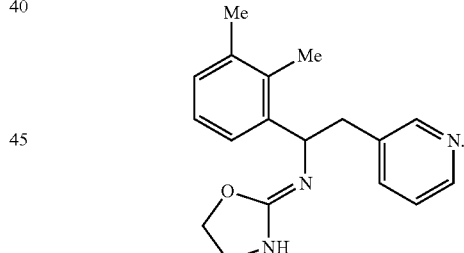

In one embodiment, there is provided an invention compound having the structure:

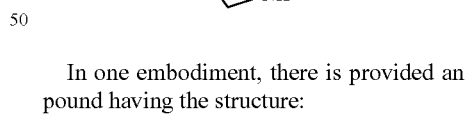

In further embodiments of the invention, there are provided compounds having the structure:

Structure 3

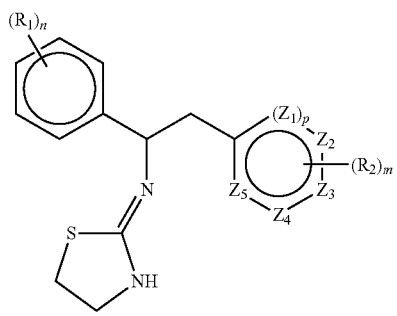

wherein:
  $Z_1$-$Z_5$ are each independently C, N, O, or S, with the proviso that at least one of $Z_1$-$Z_5$ is N;
  n and m are each independently 1 to 5;
  p is 0 or 1;
  each $R_1$ and $R_2$ is independently H, lower alkyl, halide, hydroxy, alkoxy, or trifluoromethyl;
or pharmaceutically acceptable salts thereof.

Exemplary compounds according to Structure 3 include, but are not limited to, the following structures:

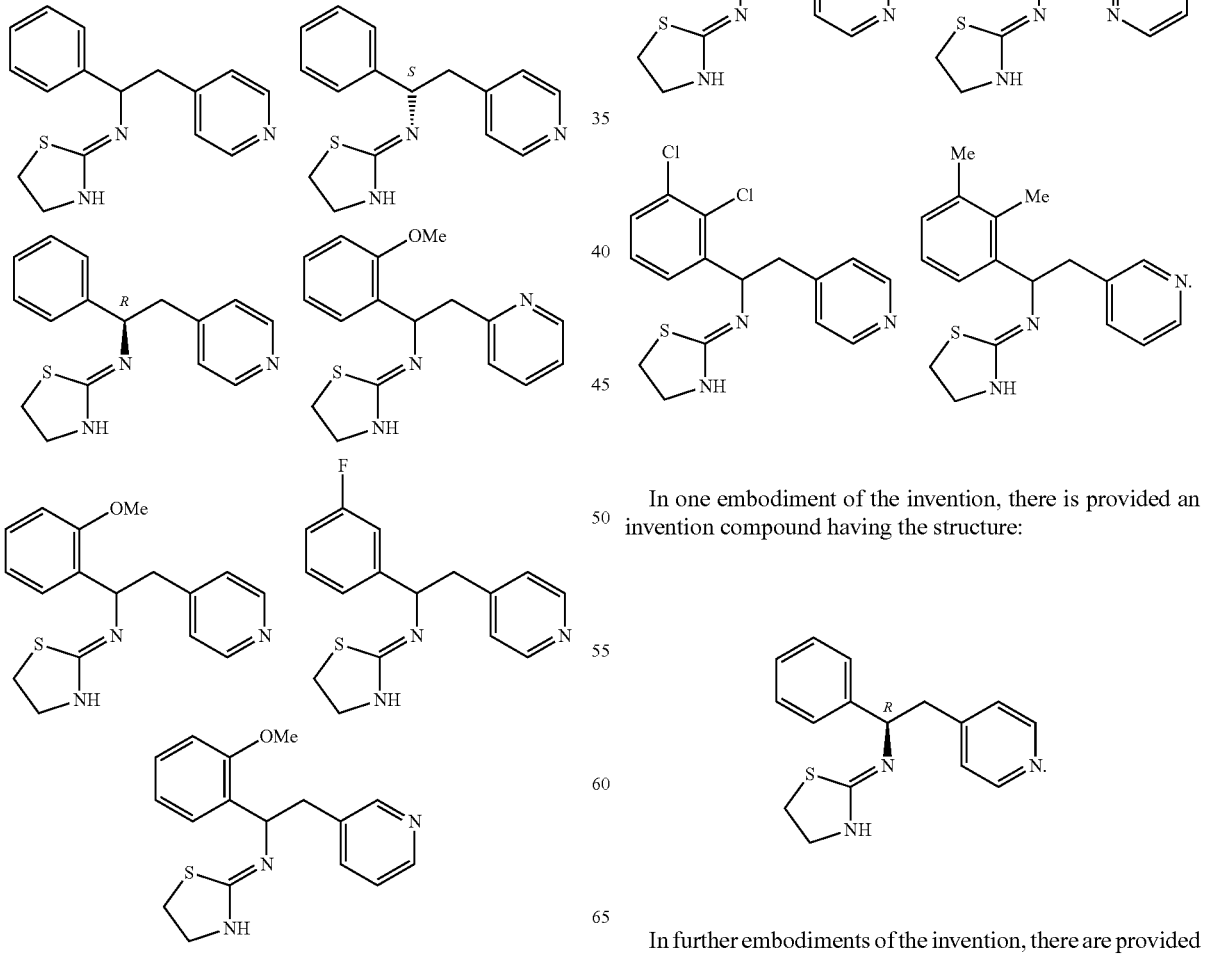

In one embodiment of the invention, there is provided an invention compound having the structure:

In further embodiments of the invention, there are provided compounds having the structure:

Structure 4

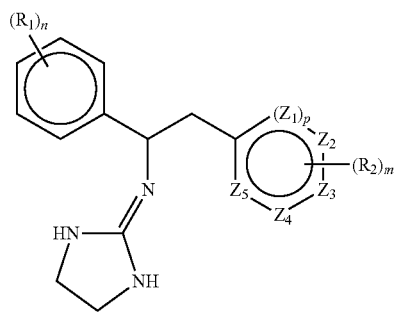

wherein:
Z₁-Z₅ are each independently C, N, O, or S, with the proviso that at least one of Z₁-Z₅ is N;
n and m are each independently 1 to 5;
p is 0 or 1;
each R₁ and R₂ is independently H, lower alkyl, halide, hydroxy, alkoxy, or trifluoromethyl;

or pharmaceutically acceptable salts thereof.

Exemplary compounds according to Structure 4 include, but are not limited to, the following structures:

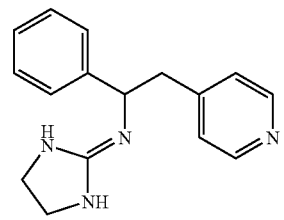 [SMILES: c1ccc(C(Cc2ccncc2)N=C2NCCN2)cc1]
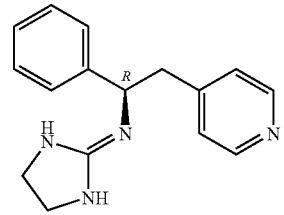
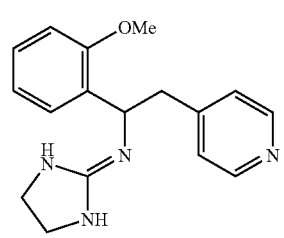 [SMILES: COc1ccccc1C(Cc1ccncc1)N=C1NCCN1]
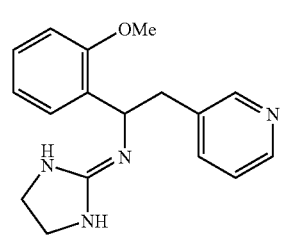

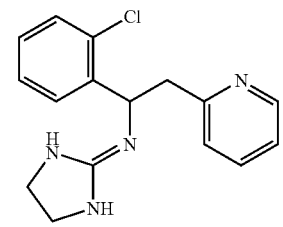
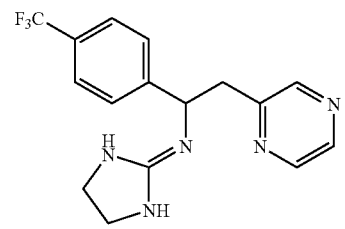
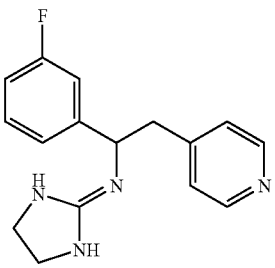
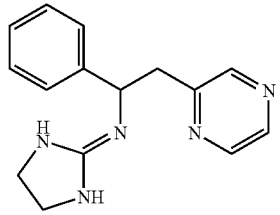 [SMILES: c1ccc(C(Cc2cnccn2)N=C2NCCN2)cc1]
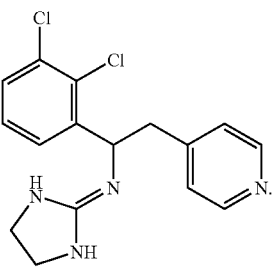
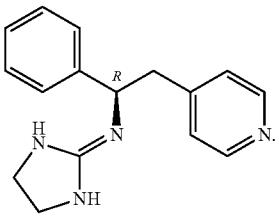

In one embodiment of the invention, there is provided an invention compound having the structure:

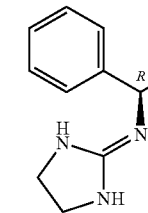

The compounds set forth herein are typically prepared by reacting appropriately substituted amines with isocyanates, isothiocyanates, or imidazole sulfonic acids. Schemes A-F outlined below describe several exemplary syntheses of the precursor amines used in preparing invention compounds. Experimental details are set forth in the Examples, vide infra.

Scheme A:
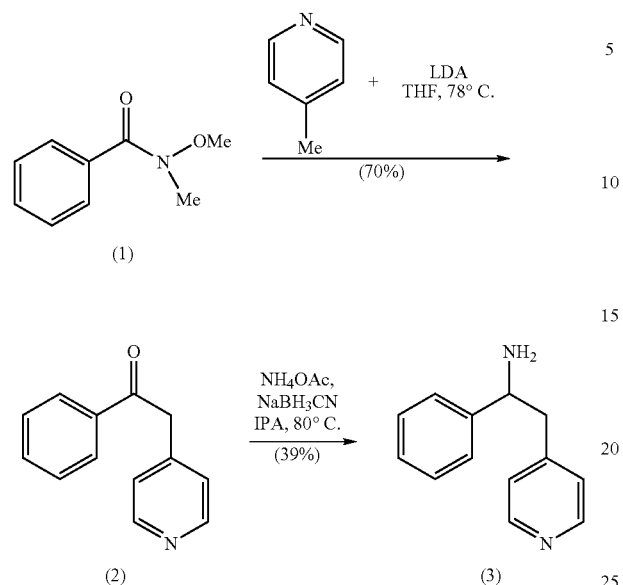
Scheme B:
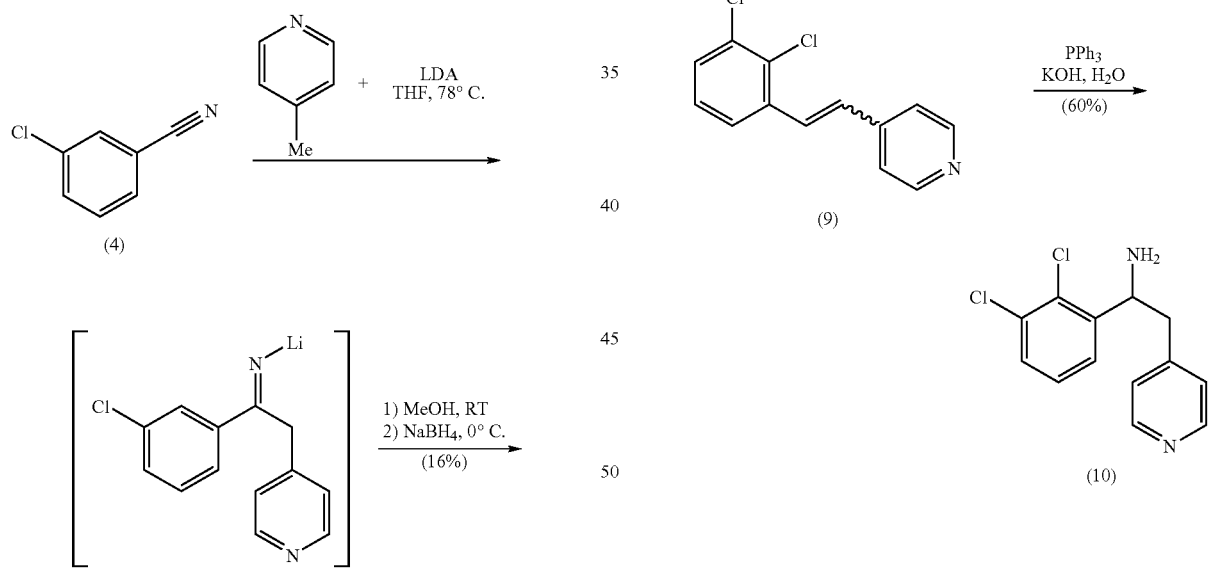
Scheme C:
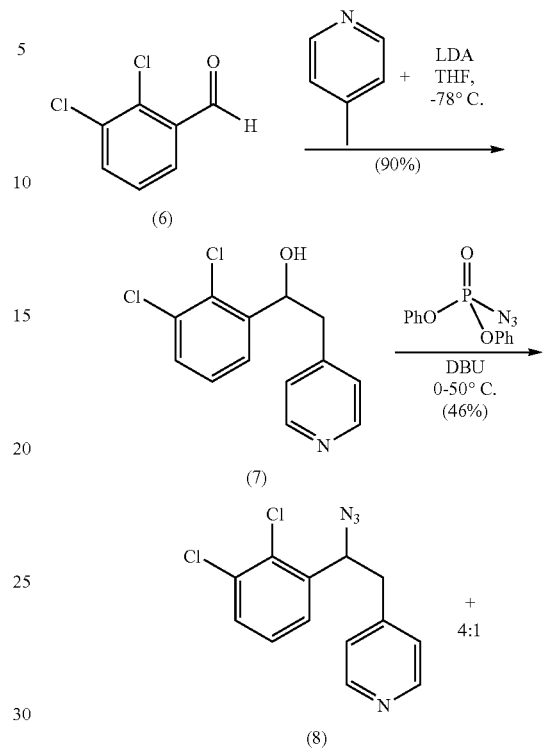
Scheme D:
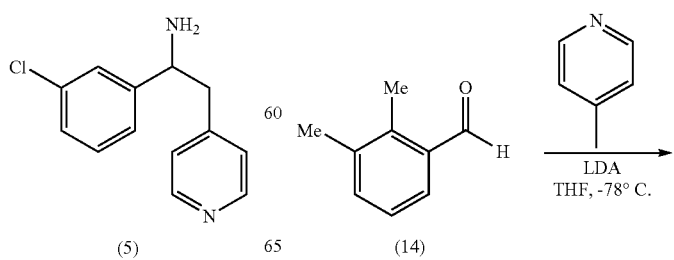

-continued
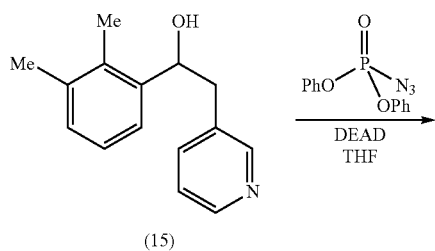
(15)
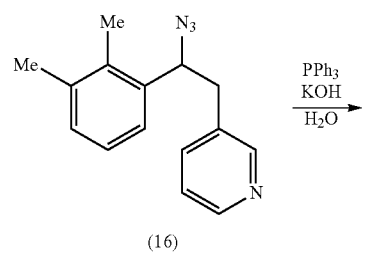
(16)
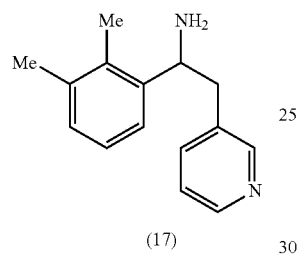
(17)
Scheme E:
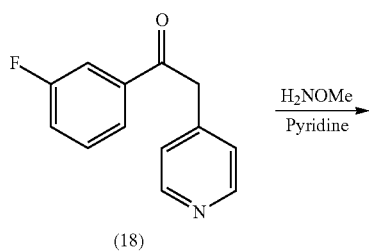
(18)
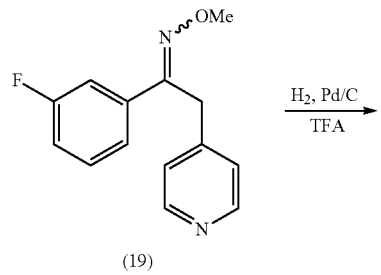
(19)
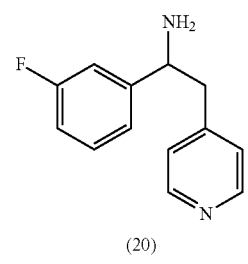
(20)
Scheme F:
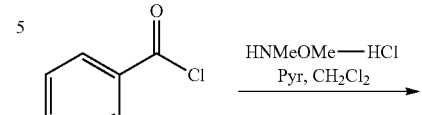
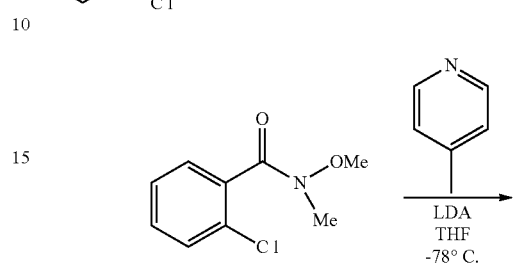
21
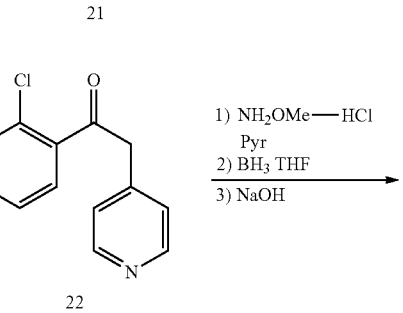
22
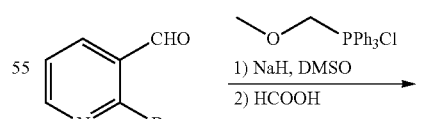
23
Coupling of the amines with either isocyanate, isothiocyanate, or imidazole sulfonic acids can be achieved as set forth below in Schemes 1-3.
Scheme G:
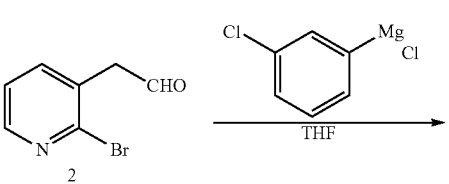

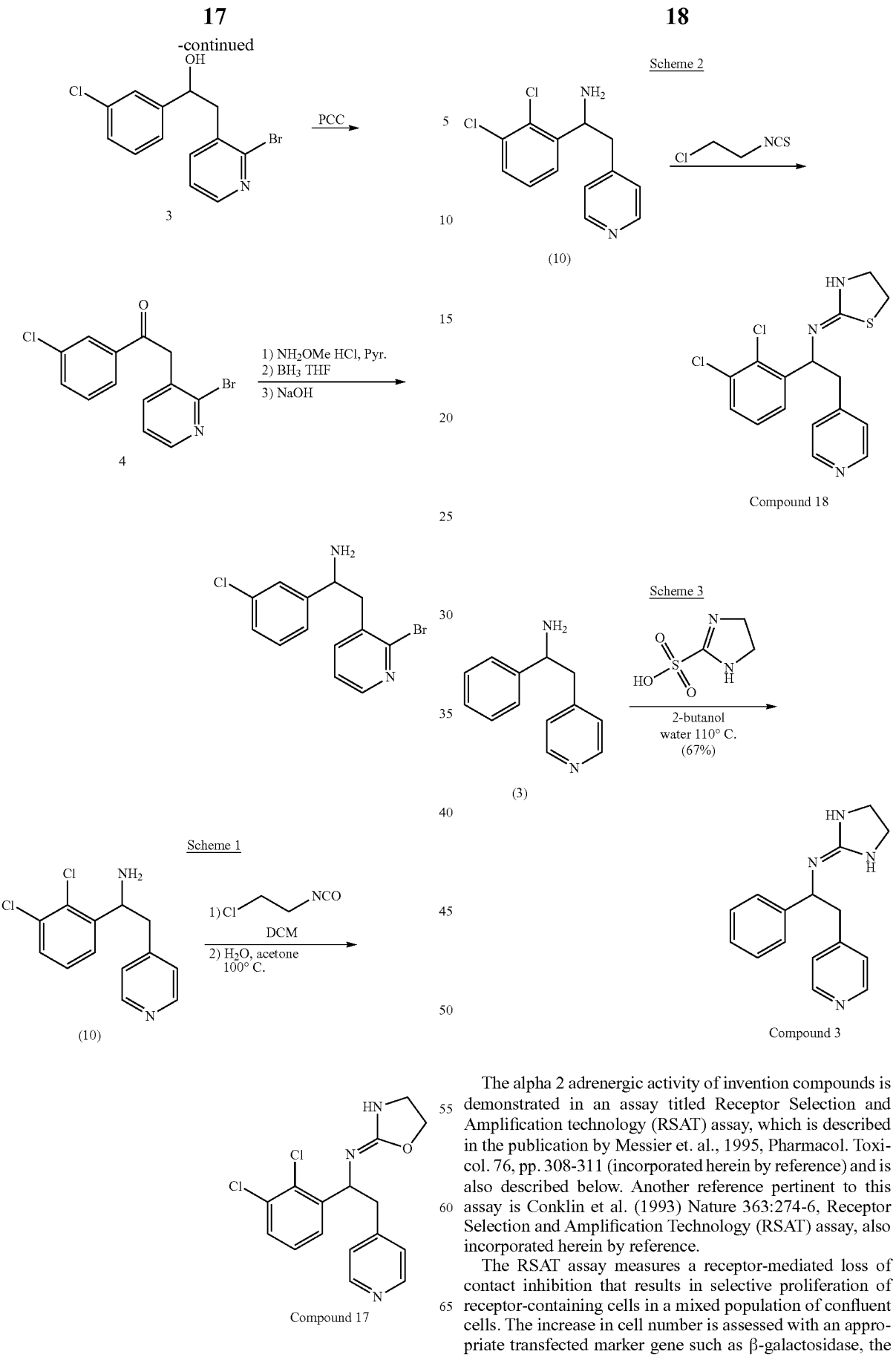

The alpha 2 adrenergic activity of invention compounds is demonstrated in an assay titled Receptor Selection and Amplification technology (RSAT) assay, which is described in the publication by Messier et. al., 1995, Pharmacol. Toxicol. 76, pp. 308-311 (incorporated herein by reference) and is also described below. Another reference pertinent to this assay is Conklin et al. (1993) Nature 363:274-6, Receptor Selection and Amplification Technology (RSAT) assay, also incorporated herein by reference.

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha 2 receptors, which normally couple to Gi, activate the RSAT response when coexpressed with a hybrid Gq protein that has a Gi receptor recognition domain, called Gq/i5.

NIH-3T3 cells are plated at a density of $2 \times 10^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μL aliquots of various concentrations of drugs in triplicate in 96-well dishes. Incubations continue 72-96 hr at 37° C. After washing with phosphate-buffered saline, β-galactosidase enzyme activity is determined by adding 200 μL of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, the chemical structure of which is shown below, is used as the standard agonist for the alpha 2B and alpha 2C receptors. The results of the RSAT assay of the compounds disclosed herein are shown in below together with the number of these exemplary compounds. NA stands for "not active" at concentrations less than 3-10 micromolar.

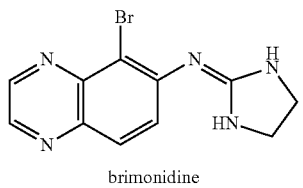

brimonidine

The compounds disclosed herein are useful for treating neurological conditions and diseases which are responsive to treatment by alpha 2 adrenergic agonists. Such conditions and diseases include, but are not limited to, pain including chronic pain (which may be, without limitation visceral, inflammatory, referred or neuropathic in origin) neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the compounds disclosed herein are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel syndrome (IBS), functional dyspepsia and ulcerative colitis. The activity of the alpha$_{2B/2C}$ specific or selective compounds disclosed herein is highly advantageous because the administration of these compounds to mammals does not result in sedation or in significant cardiovascular effects (such as changes in blood pressure or heart rate).

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (A β and A fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by A β afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

Diseases that may be treated with this invention include, but are not limited to neurodegenerative aspects of the following conditions:
MACULOPATHIES/RETINAL DEGENERATION Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration, UVEITIS/RETINITIS/CHOROIDITIS/OTHER INFLAMMATORY DISEASES Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigment Epitheliitis, Acute Macular Neuroretinopathy VASUCLAR DISEASES/EXUDATIVE DISEASES Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease TRAUMATIC/SURGICAL/ENVIRONMENTAL Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy PROLIFERATIVE DISORDERS Proliferative Vitreal Retinopathy and Epiretinal Membranes INFECTIOUS DISORDERS Ocular Histoplasmosis, Ocular Toxocariasis, Presumed Ocular Histoplasmosis Syndrome (PONS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis GENETIC DISORDERS Retinitis Pigmentosa, Systemic Disorders with Associated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum RETINAL TEARS/HOLES Retinal Detachment, Macular Hole, Giant Retinal Tear TUMORS Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

The results of the RSAT assay with several exemplary compounds of the invention are disclosed in Table 1 below, together with the chemical structures of these exemplary compounds. "Not active" means the compounds are not active at concentrations less than 10 micromolar.

| Biological Data: Intrinsic Activity potency nM efficacy (EC50) | Alpha 1A | Alpha 2B | Alpha 2C |
|---|---|---|---|
| 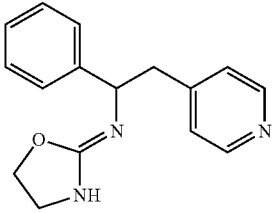<br>Compound 1 | 175 (1.20) | 8 (1.09) | 132 (0.67) |
| 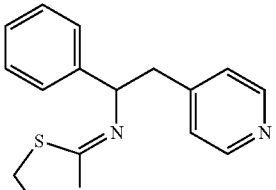<br>Compound 2 | 372 (1.45) | 10 (1.18) | 525 (0.72) |
| 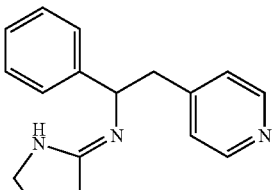<br>Compound 3 | 1190 (0.63) | 22 (1.02) | NA |
| 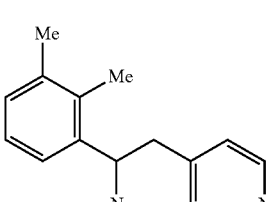<br>Compound 4 | 474 (0.77) | 3.8 (1.1) | 14 (0.63) |
| 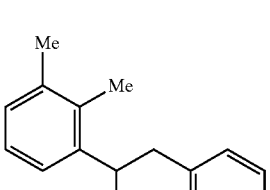<br>Compound 5 | NA | 3.1 (1.15) | 8.4 (0.49) |

-continued

| Biological Data: Intrinsic Activity potency nM efficacy (EC50) | Alpha 1A | Alpha 2B | Alpha 2C |
|---|---|---|---|
| Compound 6 (2,3-dimethylphenyl, 4-pyridyl, oxazoline) | 546 (0.88) | 2.1 (1.1) | 80 (0.68) |
| Compound 7 (2-OMe phenyl, 3-pyridyl, thiazoline) | 32 (1.7) | 12 (1.0) | 14 (0.92) |
| Compound 8 (3-Cl phenyl, 4-pyridyl, oxazoline) | 80 (1.4) | 5.2 (0.98) | 15 (0.6) |
| Compound 9 (2-OMe phenyl, 3-pyridyl, oxazoline) | 52 (1.6) | 17 (0.95) | 16 (0.91) |
| Compound 10 (2-OMe phenyl, 4-pyridyl, imidazoline) | 37 (1.0) | 11 (0.82) | 18 (0.76) |
| Compound 11 (2-OMe phenyl, 3-pyridyl, thiazoline) | 56 (1.6) | 17 (0.78) | 17 (0.86) |
| Compound 12 (2-OMe phenyl, 2-pyridyl, imidazoline) | 74 (0.92) | 10 (0.67) | 18 (0.61) |
| Compound 13 (2-OMe phenyl, 3-pyridyl, oxazoline) | 51 (1.12) | 9 (0.62) | 23 (0.66) |
| Compound 14 (phenyl, pyrazinyl, oxazoline) | 627 (1.19) | 132 (1.0) | NA |
| Compound 15 (phenyl, pyrazinyl, imidazoline) | 1300 (0.72) | 198 (0.84) | NA |
| Compound 16 (phenyl, pyrazinyl, thiazoline) | 1480 (1.1) | 170 (0.97) | 100 (0.5) |

-continued
| Biological Data: Intrinsic Activity potency nM efficacy (EC50) | Alpha 1A | Alpha 2B | Alpha 2C |
|---|---|---|---|
| 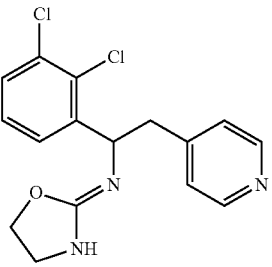  Compound 17 | 440 (1.3) | 5 (1.15) | 30 (0.65) |
| 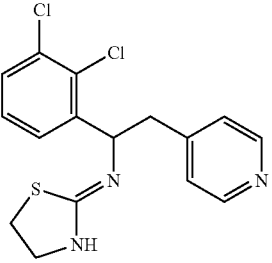 [SMILES: Clc1cccc(C(Cc2ccncc2)/N=C2/NCCS2)c1Cl]  Compound 18 | 470 (1.0) | 2 (1.1) | 21 (0.6) |
| 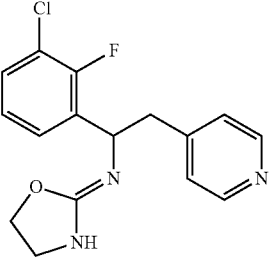 [SMILES: Fc1c(Cl)cccc1C(Cc1ccncc1)/N=C1/NCCO1]  Compound 19 | 182 (1.27) | 4 (1.3) | 11 (0.54) |
| 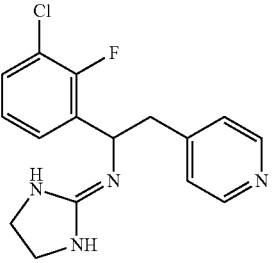 [SMILES: Fc1c(Cl)cccc1C(Cc1ccncc1)N=C1NCCN1]  Compound 20 | 670 (0.6) | 5 (1.1) | NA |
| 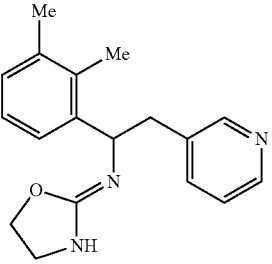 [SMILES: Cc1cccc(C(Cc2cccnc2)/N=C2/NCCO2)c1C]  Compound 21 | 742 (0.6) | 5 (1.2) | 18 (0.4) |
-continued
| Biological Data: Intrinsic Activity potency nM efficacy (EC50) | Alpha 1A | Alpha 2B | Alpha 2C |
|---|---|---|---|
| 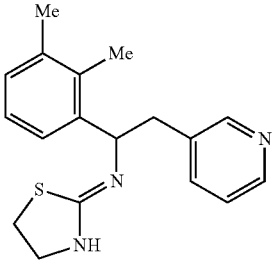 [SMILES: Cc1cccc(C(Cc2cccnc2)/N=C2/NCCS2)c1C]  Compound 22 | 374 (0.7) | 7 (1.0) | NA |
| 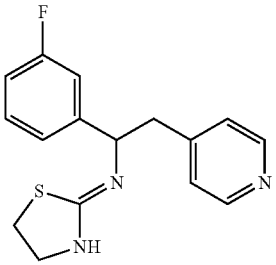 [SMILES: Fc1cccc(C(Cc2ccncc2)/N=C2/NCCS2)c1]  Compound 23 | 238 (1.36) | 9 (1.13) | 15.4 (0.79) |
| 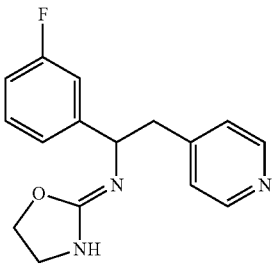 [SMILES: Fc1cccc(C(Cc2ccncc2)/N=C2/NCCO2)c1]  Compound 24 | 872 (1.1) | 14.3 (0.98) | 237 (0.93) |
| 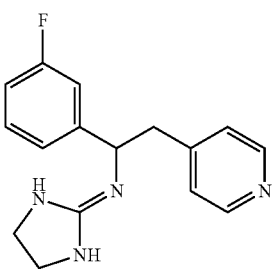 [SMILES: Fc1cccc(C(Cc2ccncc2)N=C2NCCN2)c1]  Compound 25 | 1080 (0.97) | 25 (0.68) | 16 (1.03) |
| 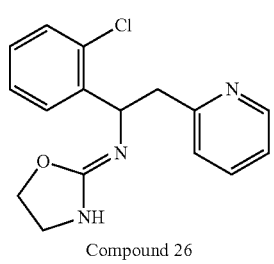  Compound 26 | 267 (1.27) | 13 (0.9) | 53 (0.87) |

| Biological Data: Intrinsic Activity potency nM efficacy (EC50) | Alpha 1A | Alpha 2B | Alpha 2C |
|---|---|---|---|
| 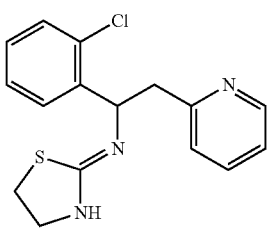 [SMILES: Clc1ccccc1C(Cc1ccccn1)/N=C1/NCCO1]  Compound 27 | 784 (1.0) | 25 (1.23) | 1260 (1.0) |
| 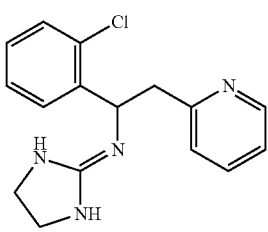 [SMILES: Clc1ccccc1C(Cc1ccccn1)N=C1NCCN1]  Compound 28 | 288 (0.88) | 49 (0.42) | 22 (0.65) |
| 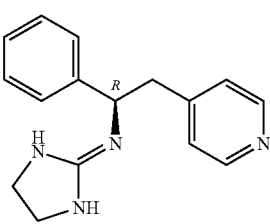  Compound 29 | 724 (0.60) | 13 (0.77) | 96 (0.60) |
| 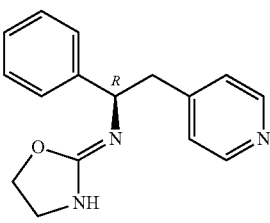  Compound 30 | 157 (1.1) | 6 (1.16) | 24 (0.78) |
| 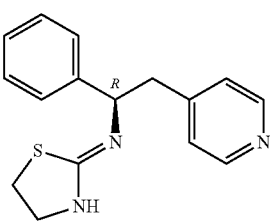  Compound 31 | 176 (1.1) | 21 (0.64) | 6.1 (1.0) |
| 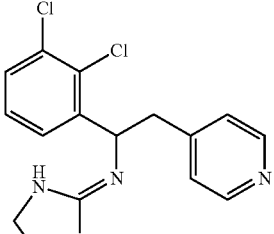  Compound 32 | 108 (0.52) | 1 (1.3) | NA | nd = no data,
NA = not active

Generally speaking, alpha 2 agonists can alleviate sympathetically-sensitized conditions that are typically associated with periods of stress. These include the neurological conditions of 1) increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha 2 agonists including alpha 2B/2C agonists are also useful in the treatment of glaucoma, elevated intraocular pressure, neurodegenerative diseases including Alzheimer's, Parkinson's, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

A compound is considered selective agonist of alpha 2B and/or alpha 2C adrenergic receptors in preference over alpha 2A receptors, if the compound is more active, preferably at least ten (10) times more active towards either alpha 2B or towards alpha 2C receptors than towards alpha 2A receptors. It can be seen from these tables that several compounds of the invention are specific or selective agonists of alpha 2B and/or alpha 2C adrenergic receptors within the former definition, and have no agonist like activity or only insignificant agonist-like activity on alpha 2A receptors. However, compounds of the invention which are active as agonists of all three alpha 2 receptors (pan agonists) are also desirable.

Thus, the compounds of the invention are useful for treating conditions and diseases which are responsive to treatment by alpha 2 and particularly by alpha 2B and/or alpha 2C adrenergic receptor agonists. Such conditions and diseases include, but are not limited to, pain including chronic pain (which may be, without limitation visceral, inflammatory, referred or neuropathic in origin), neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the compounds of this invention are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel syndrome (IBS), functional dyspepsia and ulcerative colitis.

The activity of the compounds of the invention is highly advantageous because the administration of these compounds to mammals does not result in sedation or in significant cardiovascular effects (such as changes in blood pressure or heart rate).

The compounds of the invention act and can be used as a highly effective analgesic, particularly in chronic pain models, with minimal undesirable side effects, such as sedation and cardiovascular depression, commonly seen with other agonists of the alpha 2 receptors.

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal, particularly a human being. In certain cases, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of Structure 1 in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains at least one compound of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists of alpha 2 adrenergic receptors. The compositions containing the compounds of the invention are primarily, but not exclusively, used for alleviation of chronic pain and/or allodynia. Some of the compounds of the invention have the demonstrable advantageous property that they are specific or selective to alpha 2B and/or alpha 2C adrenergic receptors in preference over alpha 2A adrenergic receptors. In addition, some of the alpha 2 agonist compounds have no or only minimal cardiovascular and/or sedatory activity.

Thus, in further embodiments of the invention, there are provided methods for treating a disorder associated with modulation of alpha 2 adrenergic receptors. Such methods can be performed, for example, by administering to a subject in need thereof a pharmaceutical composition containing a therapeutically effective amount of at least one invention compound of Structure 1. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

In some embodiments, the disorder is chronic pain, visceral pain, neuropathic pain, corneal pain, glaucoma, elevated intraocular pressure, ischemic neuropathies, neurodegenerative diseases, diarrhea, nasal congestion, muscle spasticity, diuresis, withdrawal syndromes, neurodegenerative diseases, optic neuropathy, spinal ischemia, stroke, memory and cognition deficits, attention deficit disorder, psychoses, manic disorders, anxiety, depression, hypertension, congestive heart failure, cardiac ischemia, arthritis, spondylitis, gouty arthritis, osteoarthritis, juvenile arthritis, autoimmune diseases, lupus erythematosus, chronic gastrointestinal inflammations, Crohn's disease, gastritis, irritable bowel syndrome (IBS), functional dyspepsia, ulcerative colitis, allodynia, or a combination thereof.

In one embodiment, the disorder is chronic pain. In one embodiment, the disorder is visceral pain. In one embodiment, the disorder is neuropathic pain.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

In still another embodiment of the invention, there are provided methods for treating a disorder associated with modulation of alpha 2 adrenergic receptors. Such methods can be performed, for example, by administering to a subject in need thereof a therapeutically effective amount of at least one compound of Structure 1, or any combination thereof, or pharmaceutically acceptable salts, hydrates, solvates, crystal forms, isomers, tautomers, enantiomers, and diastereomers thereof.

The following examples are intended only to illustrate the invention and should in no way be construed as limiting the invention.

EXAMPLES

Schemes A-F set forth below describe different methods to heterocyclic amines, which are precursors to the compounds of the present invention.

Part I: Preparation of Precursor Amines

Scheme A:

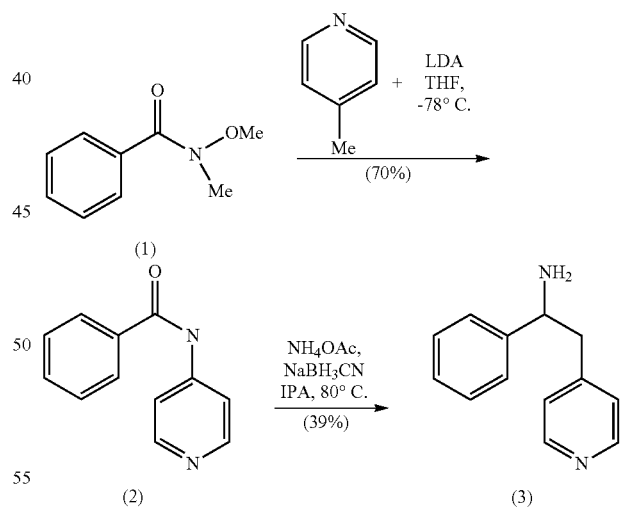

1-Phenyl-2-(pyridin-4-yl)ethanone (2): Lithium diisopropyl amide (16.9 mL, 1.5 M in cyclohexane, 25.4 mmol) was added to THF (40 mL) at −78° C. A solution of 4-picoline (2.50 mL, 25.4 mmol) in THF (30.0 mL) was added dropwise to the LDA solution. The dry ice bath was removed. The reaction mixture was stirred at 0° C. for 30 minutes, and cooled down to −78° C. A solution of N-methoxy-N-methylbenzamide (1) (5.00 g, 29.6 mmol) in THF (20.0 mL) was added dropwise. The reaction mixture was warmed to room temperature and stirred overnight. The mixture was quenched with water, and extracted with ethyl acetate (3×). The pooled organic layer was dried over magnesium sulfate. The mixture was filtered, and the solvent was removed under vacuum to give the crude product. The crude material was triturated with hot hexane, and filtered to give 1-phenyl-2-(pyridin-4-yl) ethanone (2) as a yellow solid (3.53 g, 17.9 mmol, 70% yield).

1-Phenyl-2-(pyridin-4-yl)ethanamine (3): A mixture of (2) (1.98 g, 10.0 mmol), ammonium acetate (23.2 g, 300 mmol), and sodium cyanoborohydride (4.63 g, 69.9 mmol) in IPA (100 mL) was heated at 80° C. overnight. The mixture was evaporated under reduced pressure to remove IPA. The residue was diluted with water, and basified with NaOH (2M) to pH>7. The aqueous layer was extracted with dichloromethane (3×). The pooled organic layer was removed under vacuum. The residue was purified by chromatography on silica gel (100% ethyl acetate, then 10% saturated ammonia methanol in dichloromethane) to give 1-phenyl-2-(pyridin-4-yl)ethanamine (3) as a clear oil (0.780 g, 3.94 mmol, 39% yield).

Scheme B:

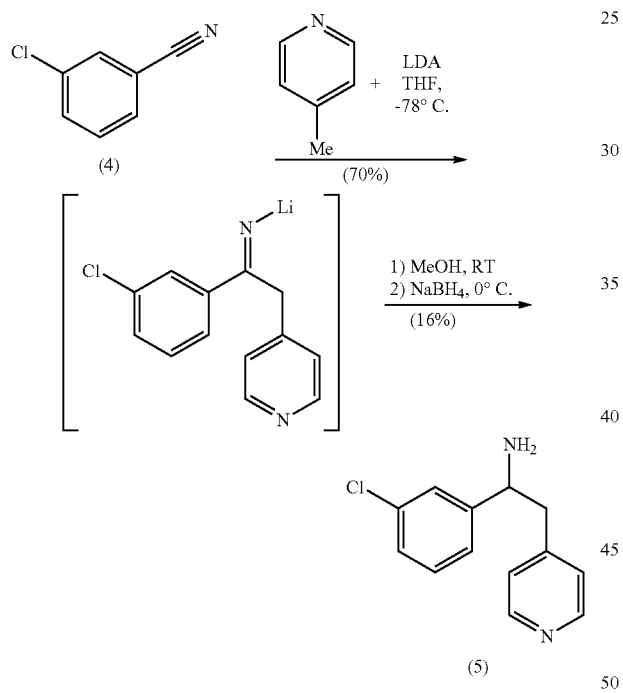

1-(3-Chlorophenyl)-2-(pyridin-4-yl)ethanamine (5): 3-chlorobenzonitrile (4) (3.14 g, 15.6 mmol) was treated similarly to (1) in Scheme A. After the reaction mixture was stirred at room temperature overnight, it was added methanol (50 mL). The resulting mixture was cooled to 0° C., and added sodium borohydride (1.46 g, 37.8 mmol). After stirring for 2 hours, more sodium borohydride (1.00 g, 25.9 mmol) was added. The reaction mixture was stirred at room temperature overnight. The mixture was evaporated under reduced pressure. The residue was quenched with water, and extracted with chloroform/isopropanol (3:1, 3×, 200 mL). The pooled organic layer was dried over magnesium sulfate. The mixture was filtered. Silica gel was added to the filtrate, and the solvents were removed under vacuum. Purification by chromatography on silica gel gave 1-(3-chlorophenyl)-2-(pyridin-4-yl)ethanamine (5) (0.96 g, 4.14 mmol, 16% yield).

Scheme C:

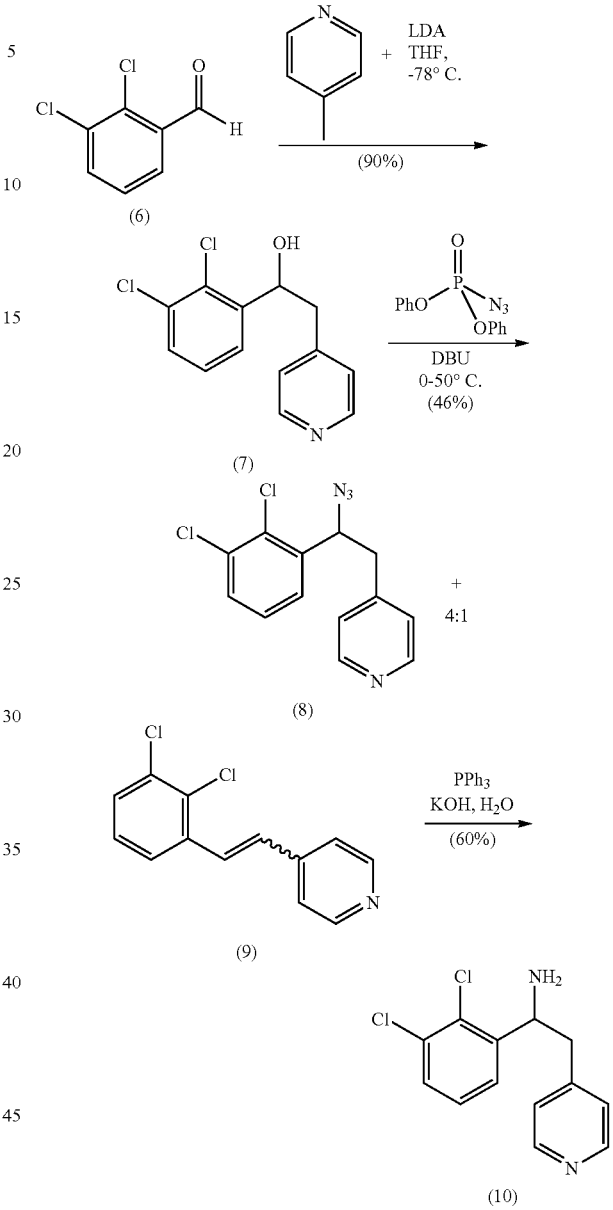

1-(2,3-Dichlorophenyl)-2-(pyridin-4-yl)ethanol (7): 2,3-dichlorobenzaldehyde (6) (4.28 g, 24.2 mmol) was treated similarly to (1) in Scheme A. The crude material was washed twice with hexane to give 1-(2,3-dichlorophenyl)-2-(pyridin-4-yl)ethanol (7) as a yellow solid (6.20 g, 23.2 mmol, 90% yield).

4-(2-Azido-2-(2,3-dichlorophenyl)ethyl)pyridine (8): 1-(2,3-dichlorophenyl)-2-(pyridin-4-yl)ethanol (7) (6.20 g, 23.2 mmol) in THF (100 mL) was added diphenyl phosphorazidate (6.00 mL, 27.8 mmol), and DBU (4.20 mL, 23.1 mmol) at 0° C. The mixture was stirred at room temperature overnight. The mixture was heated at 50° C. for 1.5 hour. The solvents were evaporated under reduced pressure. The residue was diluted with water, and extracted with ethyl acetate (3×). The pooled organic layer was dried over magnesium sulfate. The mixture was filtered. Silica gel was added to the filtrate, and the solvents were evaporated under reduce pressure. Purification by chromatography on silica gel (60% hexane, 40% ethyl acetate) gave a 4:1 mixture of products: 4-(2- azido-2-(2,3-dichlorophenyl)ethyl)pyridine (8) (4 parts, 3.82 g, 10.6 mmol, 46% yield), and 4-(2,3-dichlorostyryl)pyridine (9) (1 part).

1-(2,3-Dichlorophenyl)-2-(pyridin-4-yl)ethanamine (10): A mixture of (8) (81% pure, 3.82 g, 10.6 mmol) and (9) in THF (30 mL) was added triphenylphosphine (2.86 g, 10.9 mmol) at room temperature. After the solution was stirred for 15 minutes, potassium hydroxide (0.61 g, 10.9 mmol) in water (6 mL) was added. The resulting mixture was stirred at room temperature overnight. The mixture was acidified to pH~3 with HCl (2M). The aqueous layer was washed numerous times with diethyl ether, and basified to pH>7 with NaOH (2M). The basic layer was extracted with ethyl acetate. The pooled organic layer was dried over magnesium sulfate. The mixture was filtered. Silica gel was added to the filtrate, and the solvent was removed under vacuum. Purification by chromatography on silica gel (2 to 10% methanol in dichloromethane) gave 1-(2,3-dichlorophenyl)-2-(pyridin-4-yl) ethanamine (10) as a solid (1.71 g, 6.48 mmol, 60% yield).

Scheme D:

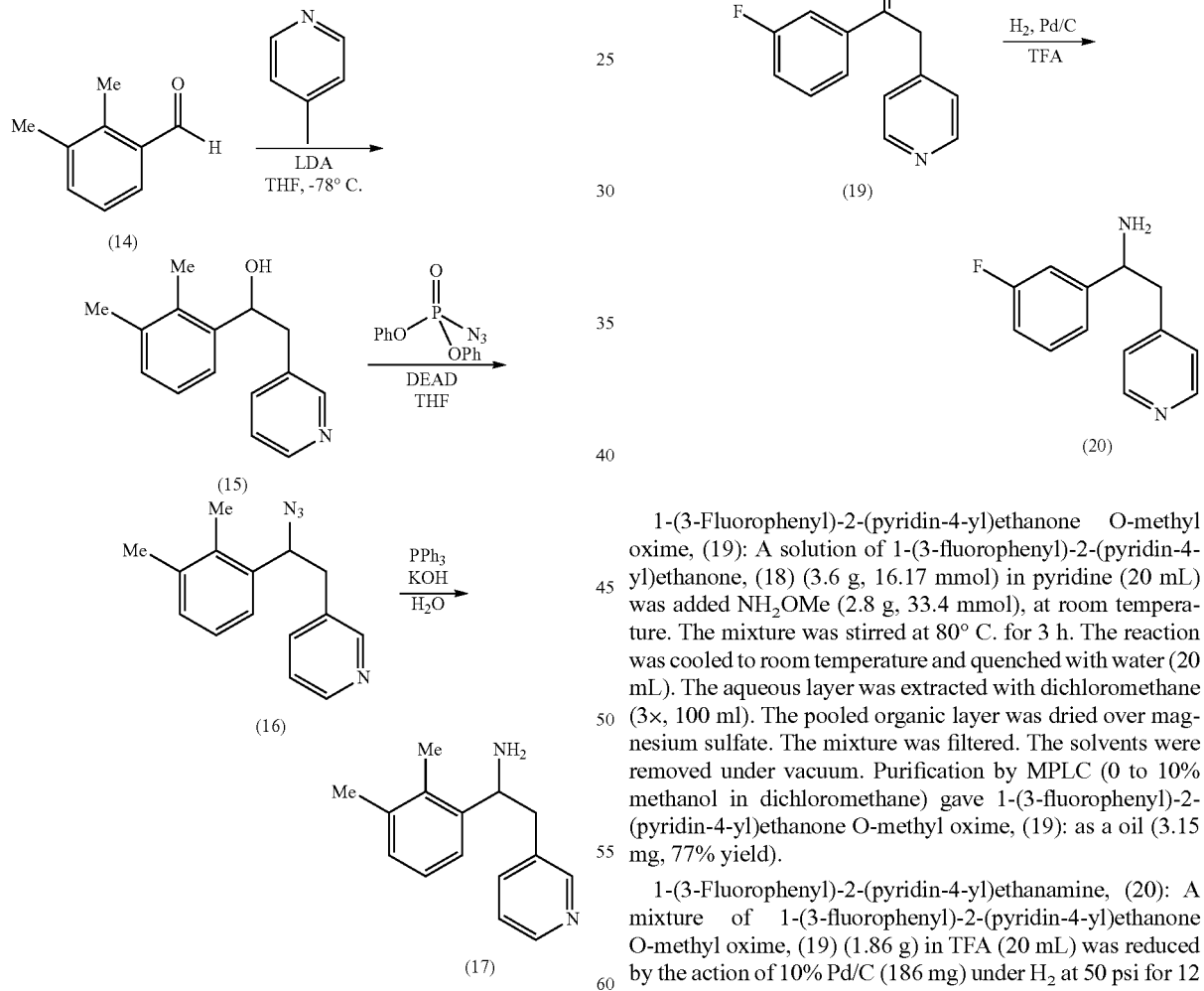

3-(2-Azido-2-(2,3-dichlorophenyl)ethyl)pyridine (16, JOC, 1999, p 6515) A solution of triphenylphosphine (1.25 g, 4.76 mmol) THF (30 mL) was treated with diethyl azodicarboxylate (DEAD) (2 mL, 40% in toluene) at room temperature. Diphenylphosphoryl azide was added dropwise followed by a THF solution of 1-(2,3-dimethylphenyl)-2-(pyridin-3-yl)ethanol, (15) (900 mg, 3.97 mmol). The mixture was stirred at room temperature overnight. The solvent was removed under vacuum. The residue was passed through silica gel chromatography using 30% EtOAc in hexane, gave 3-(2-azido-2-(2,3-dichlorophenyl)ethyl)pyridine (16), (1.5 g, impure).

Scheme E:

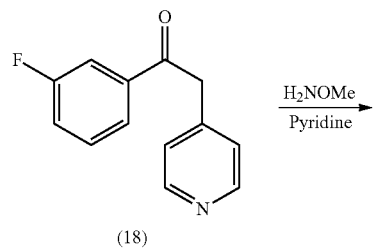

1-(3-Fluorophenyl)-2-(pyridin-4-yl)ethanone O-methyl oxime, (19): A solution of 1-(3-fluorophenyl)-2-(pyridin-4-yl)ethanone, (18) (3.6 g, 16.17 mmol) in pyridine (20 mL) was added NH$_2$OMe (2.8 g, 33.4 mmol), at room temperature. The mixture was stirred at 80° C. for 3 h. The reaction was cooled to room temperature and quenched with water (20 mL). The aqueous layer was extracted with dichloromethane (3×, 100 ml). The pooled organic layer was dried over magnesium sulfate. The mixture was filtered. The solvents were removed under vacuum. Purification by MPLC (0 to 10% methanol in dichloromethane) gave 1-(3-fluorophenyl)-2-(pyridin-4-yl)ethanone O-methyl oxime, (19): as a oil (3.15 mg, 77% yield).

1-(3-Fluorophenyl)-2-(pyridin-4-yl)ethanamine, (20): A mixture of 1-(3-fluorophenyl)-2-(pyridin-4-yl)ethanone O-methyl oxime, (19) (1.86 g) in TFA (20 mL) was reduced by the action of 10% Pd/C (186 mg) under H$_2$ at 50 psi for 12 h at rt. The mixture was filtered through Celite and freed of solvent under reduced pressure. The residue was basified using 6N KOH. The aqueous layer was extracted with EtOAc (3×, 500 mL). The pooled organic layer was dried over magnesium sulfate. The mixture was filtered. The solvents were removed under vacuum gave 1-(3-fluorophenyl)-2-(pyridin-4-yl)ethanamine, (20): as a solid (1.6 g, 97% yield).

Scheme F:

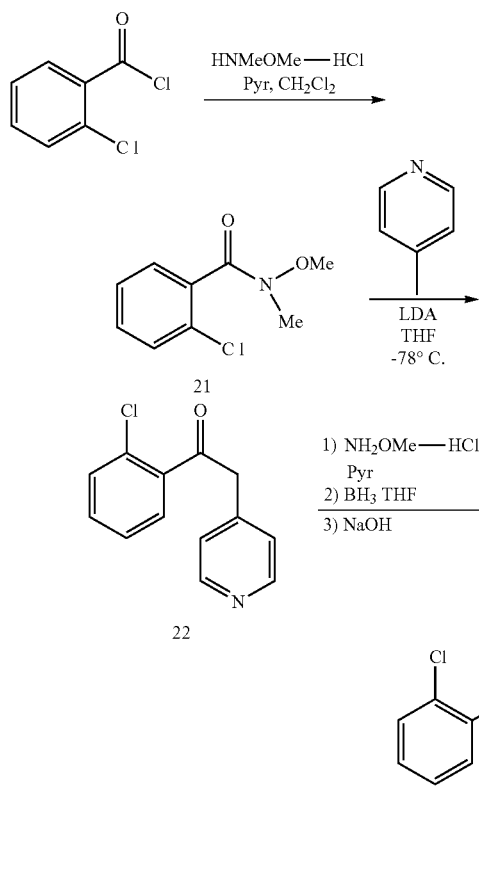

at room temperature. The resulting mixture was stirred at 50° C. for one hour. The pyridine was removed under vacuum, and residue was added water and extracted with ethyl acetate. Ethyl acetate phase was washed with brine, dried over magnesium sulfate and concentrated. Purification by chromatography on silica gel gave a mixture of geometrical oxime isomers (1.77 g, 78%) as a yellow oil. To a solution of above mixture of syn- and anti-oximes, (1.77 g, 6.8 mmol) in THF (32 mL) at room temperature was added borane-THF complex (1M, 17 mL). The resulting solution was refluxed for 3 hours, and cooled to 0° C. Water (28 mL) was carefully added followed by 20% NaOH (28 mL). The resulting biphasic mixture was refluxed overnight, and allowed to cool to room temperature. The mixture was extracted with ethyl acetate. Combined ethyl acetate phase was washed with brine, dried over magnesium sulfate and concentrated to give 1-(2-chlorophenyl)-2-(pyridin-4-yl)ethanamine (23) (1.2 g 76%) as yellow oil.

Preparation of Precursor Amines

Scheme G:

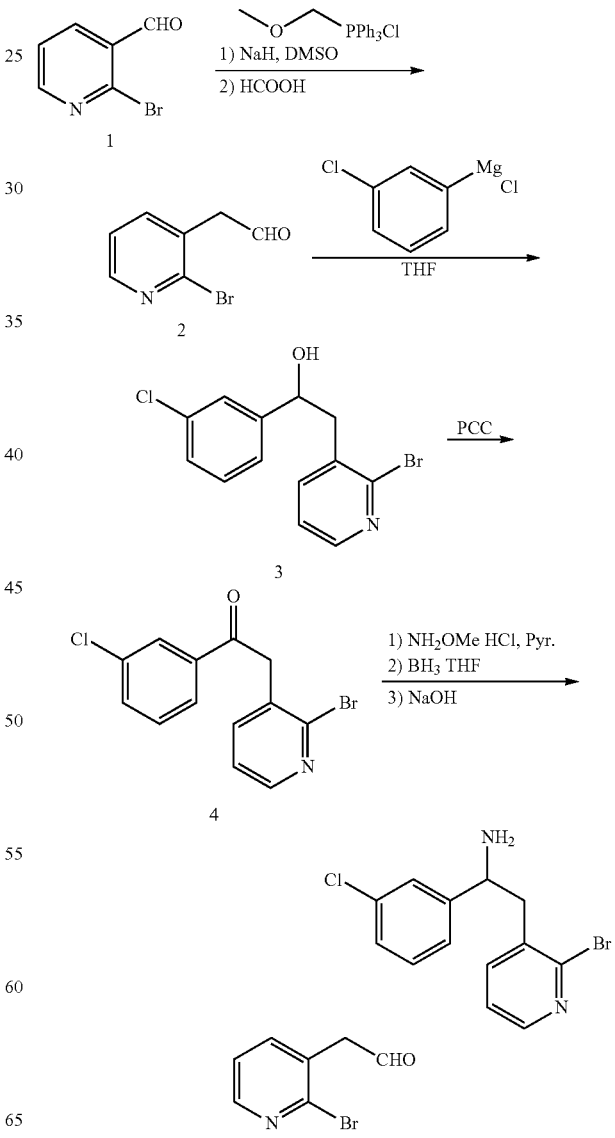

2-Chloro-N-methoxy-N-methylbenzamide (21) To a solution of 2-chlorobenzoyl chloride (8 g, 46 mmol) in dichloromethane (200 mL) at 0° C. was added N,O-dimethylhydroxylamine hydrochloride (4.9 g, 50 mmol) followed by pyridine (11 mL, 137 mmol). The mixture was stirred at room temperature for 16 hours. Water was added to the reaction mixture and organic layer was washed with brine, dried over magnesium sulfate and concentrated. Purification by chromatography on silica gel gave 2-chloro-N-methoxy-N-methylbenzamide (21) (7.8 g, 39.2 mmol, 85%) as clear oil.

1-(2-Chlorophenyl)-2-(pyridin-4-yl)ethanone (22): To lithium diisopropyl amide (6.5 mL, 1.6 M in cyclohexane, 10.4 mmol) in THF (20.0 mL) at −78° C. was added a solution of 4-picoline (1.07 g mL, 11.5 mmol) in THF (10.0 mL) dropwise. The dry ice bath was removed. The reaction mixture was stirred at 0° C. for 30 minutes, and cooled back to −78° C. A solution of 2-chloro-N-methoxy-N-methylbenzamide (21) (2.39 g, 12 mmol) in THF (10.0 mL) was added dropwise. The reaction mixture was warmed to room temperature and stirred overnight. White solid was filtered off and dissolved in ethyl acetate. The organic phase was washed with water, brine, dried over dried magnesium sulfate and concentrated under vacuum to give 1-(2-chlorophenyl)-2-(pyridin-4-yl)ethanone (22) (1.09 g, 4.7 mmol, 47%) as white solid.

1-(2-Chlorophenyl)-2-(pyridin-4-yl)ethanamine (23) To a solution of 1-(2-chlorophenyl)-2-(pyridin-4-yl)ethanone (22) (2.0 g, 8.7 mmol) in pyridine (24 mL) was added methoxylamine hydrochloride (1.45 g, 17.4 mmol) in one portion 2-(2-Bromopyridin-3-yl)acetaldehyde: To a white suspension of sodium hydride (1.36 g, 34 mmol) in DMSO (16 mL) at room temperature was added clear solution of (methoxymethyl)triphenyl)phosphonium chloride in DMSO (40 mL). The mixture became a yellow suspension. To the above suspension was added 2-bromonicotinaldehyde (2.48 g, 13.3 mmol) in DMSO (16 mL) dropwise. The mixture was stirred at room temperature for 20 hours then treated with excess sodium bicarbonate (sat), extracted with ether. The combined ether layer was washed with brine, dried over magnesium sulfate and concentrated. Purification by chromatography on silica gel gave E and Z mixture of 2-bromo-3-(2-methoxyvinyl)pyridine (1.88 g, 66%) as yellow oil.

A solution of E and Z mixture of 2-bromo-3-(2-methoxyvinyl)pyridine (1.88 g, 8.79 mmol) in formic acid (96%, 10 mL) was stirred at 60° C. for 16 hours and at 80° C. for 3 hours before cooled to room temperature. Most of formic acid was removed. The mixture was diluted with ethyl acetate, washed with sodium bicarbonate and brine, dried over magnesium sulfate and concentrated. Purification by chromatography on silica gel gave 2-(2-bromopyridin-3-yl)acetaldehyde (864 mg, 53% yield) as yellow solid.

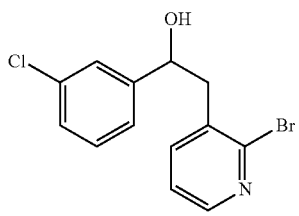 [SMILES: OC(Cc1cccnc1Br)c1cccc(Cl)c1]

2-(2-Bromopyridin-3-yl)-1-(3-chlorophenyl)ethanol: To 2-(2-bromopyridin-3-yl)acetaldehyde (864 mg, 4.7 mmol) in THF (10 mL) at 0° C. was added (3-chlorophenyl)magnesium chloride (0.5M in THF, 14 mL, 7.04 mmol). The mixture was stirred at room temperature for 4 hours then treated with ammonium chloride (sat) at 0° C., extracted with ethyl acetate. The combined ethyl acetate layer was washed with brine, dried over magnesium sulfate and concentrated. Purification by chromatography on silica gel gave 2-(2-bromopyridin-3-yl)-1-(3-chlorophenyl)ethanol (490 mg, 35% yield) as white solid.

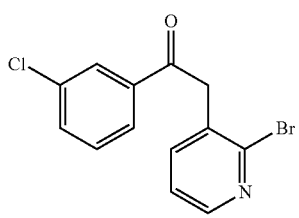 [SMILES: O=C(Cc1cccnc1Br)c1cccc(Cl)c1]

2-(2-Bromopyridin-3-yl)-1-(3-chlorophenyl)ethanone: To a vigorously stirred solution of pyridinium chlorochromate and celite in dichloromethane (20 mL) at room temperature was added a solution of 2-(2-bromopyridin-3-yl)-1-(3-chlorophenyl)ethanol in dichloromethane (10 mL). The mixture was stirred at room temperature for 3 hours then filtered through a plug of silica gel, eluted well with dichloromethane and concentrated in vacuo. Purification by chromatography on silica gel gave 2-(2-bromopyridin-3-yl)-1-(3-chlorophenyl)ethanone (313 mg, 64% yield) as white solid.

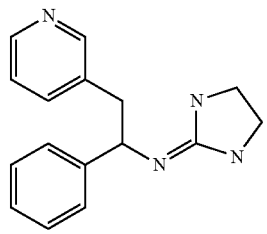 [SMILES: c1ccc(C(Cc2cccnc2)N=C2NCCN2)cc1]

N-(Imidazolidin-2-ylidene)-1-phenyl-2-(pyridin-3-yl)ethanamine (Schemes G and F) $^1$H NMR (300 MHz, CD$_3$OD): δ 8.33-8.39 (m, 2H), 7.67-7.70 (m, 1H), 7.26-7.36 (m, 6H), 4.71-4.76 (m, 1H), 3.54 (s, 4H), 3.15-3.18 (m, 2H)

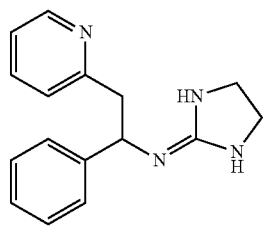 [SMILES: c1ccc(C(Cc2ccccn2)N=C2NCCN2)cc1]

N-(Imidazolidin-2-ylidene)-1-phenyl-2-(pyridin-2-yl)ethanamine (Schemes G and F) $^1$H NMR (300 MHz, CD$_3$OD): δ 8.51-8.53 (m, 1H), 7.66-7.72 (m, 1H), 7.25-7.35 (m, 6H), 7.17-7.19 (m, 1H), 4.97-5.01 (m, 1H), 3.61 (s, 4H), 3.28-3.30 (m, 2H)

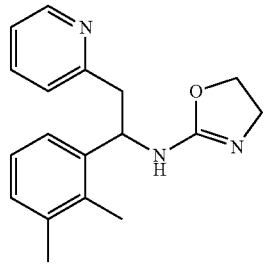 [SMILES: Cc1cccc(C(Cc2ccccn2)NC2=NCCO2)c1C]

N-(1-(2,3-Dimethylphenyl)-2-(pyridin-2-yl)ethyl)-4,5-dihydrooxazol-2-amine (Schemes G and F) $^1$H NMR (300 MHz, CDCl$_3$): δ 8.53-8.54 (m, 1H), 7.48-7.51 (m, 1H), 7.10-7.12 (m, 1H), 6.99-7.05 (m, 3H), 6.91-6.93 (m, 1H), 5.32-5.35 (m, 1H), 4.15-4.19 (m, 2H), 3.65-3.68 (m, 2H), 3.21-3.24 (m, 1H), 3.07-3.11 (m, 1H), 2.30 (s, 3H), 2.27 (s, 3H)

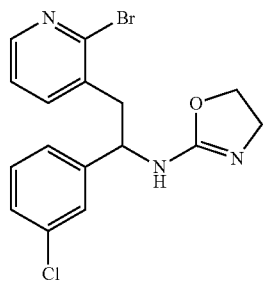

N-(2-(2-Bromopyridin-3-yl)-1-(3-chlorophenyl)ethyl)-4,5-dihydrooxazol-2-amine (Schemes G and F) $^1$H NMR (300

MHz, CDCl$_3$): δ 8.26-8.28 (m, 1H), 7.65-7.68 (m, 1H), 7.37 (s, 1H), 7.27-7.29 (m, 3H), 7.19-7.23 (m, 1H), 4.98-5.03 (m, 1H), 4.30-4.38 (m, 2H), 3.66-3.72 (m, 2H), 3.17-3.20 (m, 2H)

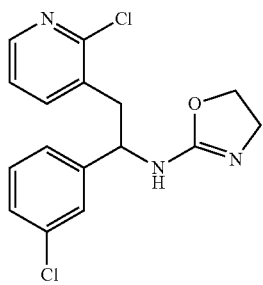

N-(1-(3-Chlorophenyl)-2-(2-chloropyridin-3-yl)ethyl)-4,5-dihydrooxazol-2-amine (Schemes G and F) $^1$H NMR (300 MHz, CDCl$_3$): δ 8.26-8.28 (m, 1H), 7.50-7.53 (m, 1H), 7.35 (s, 1H), 7.18-7.28 (m, 3H), 7.10-7.14 (m, 1H), 4.94-4.99 (m, 1H), 4.09-4.20 (m, 2H), 3.60-3.65 (m, 2H), 3.10-3.15 (m, 2H)

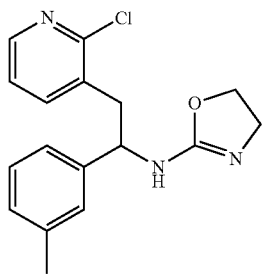 [SMILES: Cc1cccc(C(Cc2cccnc2Cl)NC2=NCCO2)c1]

N-(2-(2-Chloropyridin-3-yl)-1-m-tolylethyl)-4,5-dihydrooxazol-2-amine (Schemes G and F) $^1$H NMR (300 MHz, CD$_3$OCD$_3$): δ 8.24-8.26 (m, 1H), 7.80-7.83 (m, 1H), 7.19-7.30 (m, 4H), 7.07-7.09 (m, 1H), 5.03-5.08 (m, 1H), 4.16-4.24 (m, 2H), 3.54-3.60 (m, 2H), 3.19-3.23 (m, 2H), 2.32 (s, 3H)

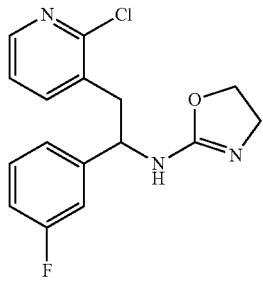

N-(2-(2-Chloropyridin-3-yl)-1-(3-fluorophenyl)ethyl)-4,5-dihydrooxazol-2-amine (Schemes G and F) $^1$H NMR (300 MHz, CD$_3$OD): δ 8.22-8.24 (m, 1H), 7.66-7.69 (m, 1H), 7.27-7.36 (m, 2H), 7.00-7.16 (m, 2H), 6.94-7.00 (m, 1H), 4.90-4.95 (m, 1H), 4.17-4.22 (m, 2H), 3.51-3.57 (m, 2H), 3.05-3.22 (m, 2H)

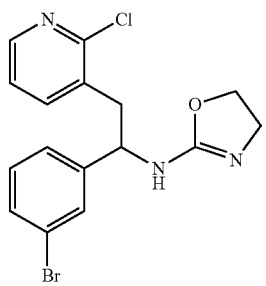

N-(1-(3-Bromophenyl)-2-(2-chloropyridin-3-yl)ethyl)-4,5-dihydrooxazol-2-amine (Schemes G and F) $^1$H NMR (300 MHz, CD$_3$OD): δ 8.22-8.25 (m, 1H), 7.65-7.68 (m, 1H), 7.51-7.52 (m, 1H), 7.40-7.43 (m, 1H), 7.21-7.40 (m, 3H), 4.87-4.92 (m, 1H), 4.22-4.27 (m, 2H), 3.54-3.60 (m, 2H), 3.06-3.22 (m, 2H)

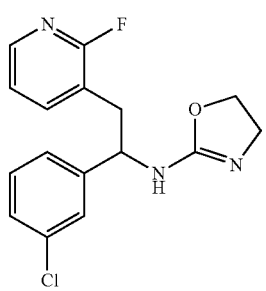

N-(1-(3-Chlorophenyl)-2-(2-fluoropyridin-3-yl)ethyl)-4,5-dihydrooxazol-2-amine (Schemes G and F) $^1$H NMR (300 MHz, CD$_3$OCD$_3$): δ 8.05-8.08 (m, 1H), 7.78-7.84 (m, 1H), 7.47 (s, 1H), 7.31-7.35 (m, 2H), 7.19-7.29 (m, 2H), 4.96-5.01 (m, 1H), 4.10-4.17 (m, 2H), 3.50-3.53 (m, 2H), 3.12-3.16 (m, 2H)

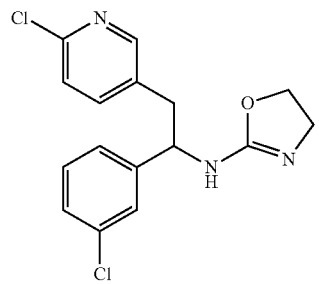 [SMILES: Clc1cccc(C(Cc2ccc(Cl)nc2)NC2=NCCO2)c1]

N-(1-(3-Chlorophenyl)-2-(6-chloropyridin-3-yl)ethyl)-4,5-dihydrooxazol-2-amine (Schemes G and F) $^1$H NMR (300 MHz, CD$_3$OCD$_3$): δ 8.28 (s, 1H), 7.74-7.76 (m, 1H), 7.49 (s, 1H), 7.33-7.38 (m, 3H), 7.27-7.31 (m, 1H), 4.92-4.95 (m, 1H), 4.12-4.18 (m, 2H), 3.52-3.57 (m, 2H), 3.10-3.18 (m, 2H)

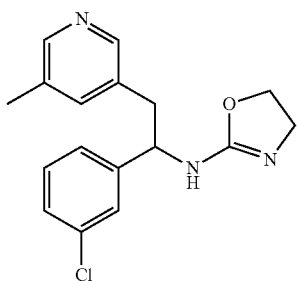 [SMILES: Cc1cncc(CC(NC2=NCCO2)c2cccc(Cl)c2)c1]

N-(1-(3-Chlorophenyl)-2-(5-methylpyridin-3-yl)ethyl)-4, 5-dihydrooxazol-2-amine (Schemes G and F) ¹H NMR (300 MHz, CD₃OCD₃): δ 8.24-8.25 (m, 2H), 7.45-7.47 (m, 2H), 7.30-7.35 (m, 2H), 7.25-7.27 (m, 1H), 4.88-4.93 (m, 1H), 4.08-4.14 (m, 2H), 3.50-3.56 (m, 2H), 3.04-3.09 (m, 2H), 2.27 (s, 3H)

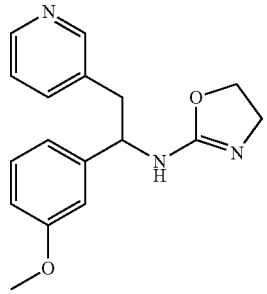

N-(1-(3-Methoxyphenyl)-2-(pyridin-3-yl)ethyl)-4,5-dihydrooxazol-2-amine (Schemes G and F) ¹H NMR (300 MHz, CD₃OCD₃): δ 8.37-8.42 (m, 2H), 7.59-7.63 (m, 1H), 7.18-7.25 (m, 2H), 6.94-6.99 (m, 2H), 6.77-6.81 (m, 1H), 4.85-4.90 (m, 1H), 4.05-4.10 (m, 2H), 3.76 (s, 3H), 3.50-3.56 (m, 2H), 3.03-3.19 (m, 2H)

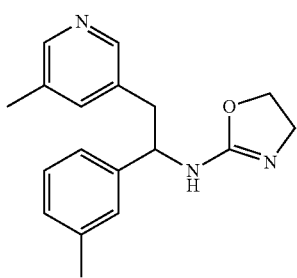 [SMILES: Cc1cncc(CC(NC2=NCCO2)c2cccc(C)c2)c1]

N-(2-(5-Methylpyridin-3-yl)-1-m-tolylethyl)-4,5-dihydrooxazol-2-amine (Schemes G and F) ¹H NMR (300 MHz, CD₃OCD₃): δ 8.23-8.25 (m, 2H), 7.47 (s 1H), 7.18-7.24 (m, 3H), 7.04-7.07 (m, 1H), 4.85-4.91 (m, 1H), 4.12-4.18 (m, 2H), 3.53-3.59 (m, 2H), 3.08-3.16 (m, 1H), 2.97-3.04 (m, 1H), 2.30 (s, 3H), 2.26 (s, 3H)

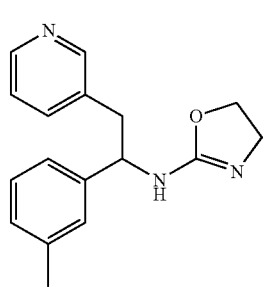

N-(2-(Pyridin-3-yl)-1-m-tolylethyl)-4,5-dihydrooxazol-2-amine (Schemes G and F) ¹H NMR (300 MHz, CD₃OD): δ 8.30-8.34 (m, 2H), 7.67-7.71 (m, 1H), 7.29-7.33 (m, 1H), 7.03-7.20 (m, 4H), 4.70-4.75 (m, 1H), 4.14-4.19 (m, 2H), 3.52-3.58 (m, 2H), 3.02-3.05 (m, 2H), 2.30 (s, 3H)

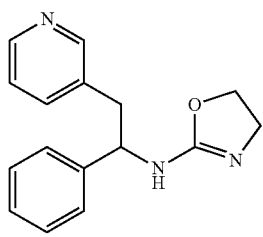 [SMILES: c1ccc(C(Cc2cccnc2)NC2=NCCO2)cc1]

N-(1-Phenyl-2-(pyridin-3-yl)ethyl)-4,5-dihydrooxazol-2-amine (Schemes G and F) ¹H NMR (300 MHz, CD₃OCD₃): δ 8.37-8.42 (m, 2H), 7.59-7.63 (m, 1H), 7.38-7.41 (m, 2H), 7.20-7.33 (m, 4H), 4.87-4.92 (m, 1H), 4.04-4.10 (m, 2H), 3.49-3.55 (m, 2H), 3.03-3.20 (m, 2H)

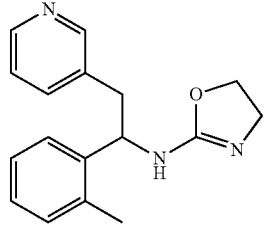 [SMILES: Cc1ccccc1C(Cc1cccnc1)NC1=NCCO1]

N-(2-(Pyridin-3-yl)-1-o-tolylethyl)-4,5-dihydrooxazol-2-amine (Schemes G and F) ¹H NMR (300 MHz, CD₃OCD₃): δ 8.38-8.42 (m, 2H), 7.52-7.60 (m, 2H), 7.18-7.24 (m, 2H), 7.07-7.15 (m, 2H), 5.11-5.16 (m, 1H), 4.04-4.10 (m, 2H), 3.48-3.55 (m, 2H), 3.08-3.16 (m, 1H), 2.95-3.02 (m, 1H), 2.29 (s, 3H)

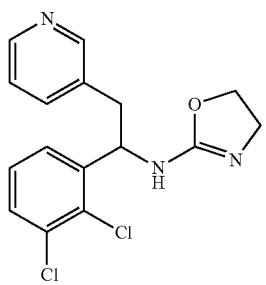 [SMILES: Clc1cccc(C(Cc2cccnc2)NC2=NCCO2)c1Cl]

N-(1-(2,3-Dichlorophenyl)-2-(pyridin-3-yl)ethyl)-4,5-dihydrooxazol-2-amine (Schemes G and F) ¹H NMR (300 MHz, CD₃OD): δ 8.43-8.44 (m, 1H), 8.38-8.40 (m, 1H), 7.78-7.82 (m, 1H), 7.43-7.48 (m, 2H), 7.29-7.40 (m, 2H), 5.20-5.25 (m, 1H), 4.16-4.21 (m, 2H), 3.49-3.54 (m, 2H), 3.10-3.17 (m, 1H), 2.82-2.90 (m, 1H)

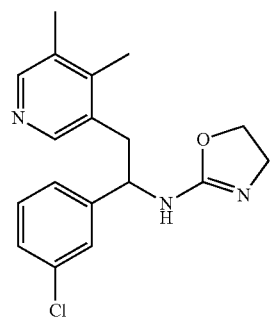

N-(1-(3-Chlorophenyl)-2-(4,5-dimethylpyridin-3-yl)ethyl)-4,5-dihydrooxazol-2-amine amine (Schemes G and F) ¹H NMR (300 MHz, CD₃OD): δ 8.10 (s, 1H), 7.97 (s, 1H), 7.18-7.31 (m, 4H), 4.69-4.74 (m, 1H), 4.16-4.22 (m, 2H), 3.52-3.57 (m, 2H), 3.04-3.07 (m, 2H), 2.28 (s, 3H), 2.29 (s, 3H)

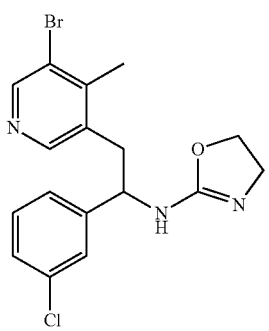

N-(2-(5-Bromo-4-methylpyridin-3-yl)-1-(3-chlorophenyl)ethyl)-4,5-dihydrooxazol-2-amine (Schemes G and F) ¹H NMR (300 MHz, CD₃OD): δ 8.46 (s, 1H), 8.11 (s, 1H), 7.20-734 (m, 4H), 4.73-4.77 (m, 1H), 4.18-4.23 (m, 2H), 3.52-3.58 (m, 2H), 3.10-3.13 (m, 2H), 2.45 (s, 3H)

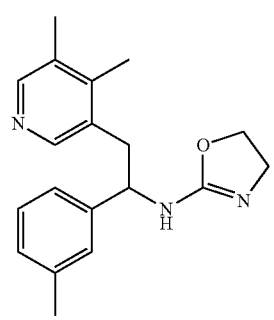

N-(2-(4,5-Dimethylpyridin-3-yl)-1-m-tolylethyl)-4,5-dihydrooxazol-2-amine (Schemes G and F) ¹H NMR (300 MHz, CD₃OCD₃): δ 8.12 (s, 1H), 8.07 (s, 1H), 7.14-7.17 (m, 3H), 7.03-7.06 (m, 1H), 4.80-4.85 (m, 1H), 4.06-4.13 (m, 2H), 3.51-3.57 (m, 2H), 3.17-3.24 (m, 1H), 2.99-3.06 (m, 1H), 2.29 (s, 3H), 2.26 (s, 3H), 2.23 (s, 3H)

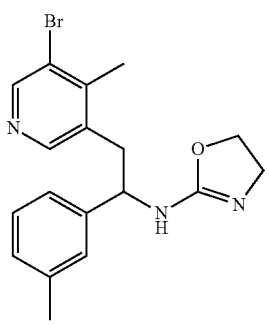 [SMILES: Cc1cccc(C(Cc2cncc(Br)c2C)NC2=NCCO2)c1]

N-(2-(5-Bromo-4-methylpyridin-3-yl)-1-m-tolylethyl)-4,5-dihydrooxazol-2-amine (Schemes G and F) ¹H NMR (300 MHz, CD₃OCD₃): δ 8.45 (s, 1H), 8.18 (s, 1H), 7.17-7.22 (m, 3H), 7.06-7.08 (m, 1H), 4.85-4.90 (m, 1H), 4.10-4.16 (m, 2H), 3.57 (br, 2H), 3.26-3.34 (m, 1H), 3.09-3.16 (m, 1H), 2.44 (s, 3H), 2.30 (s, 3H)

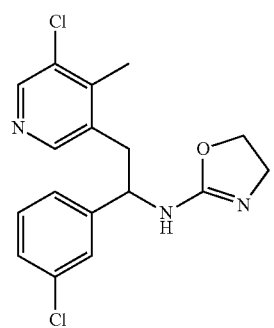

N-(2-(5-Chloro-4-methylpyridin-3-yl)-1-(3-chlorophenyl)ethyl)-4,5-dihydrooxazol-2-amine (Schemes G and F) ¹H NMR (300 MHz, CD₃OD): δ 8.33 (s, 1H), 8.10 (s, 1H), 7.20-7.34 (m, 4H), 4.73-4.77 (m, 1H), 4.16-4.21 (m, 2H), 3.51-3.57 (m, 2H), 3.09-3.11 (m, 2H), 2.42 (s, 3H)

47

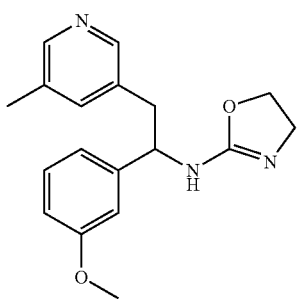 [SMILES: COc1cccc(C(Cc2cncc(C)c2)NC2=NCCO2)c1]

N-(1-(3-Methoxyphenyl)-2-(5-methylpyridin-3-yl)ethyl)-4,5-dihydrooxazol-2-amine (Schemes G and F) $^1$H NMR (300 MHz, CD$_3$O CD$_3$): δ 8.21-8.23 (m, 2H), 7.43-7.44 (m, 1H), 7.21-7.24 (m, 1H), 6.94-7.18 (m, 2H), 6.77-6.81 (m, 1H), 4.84-4.89 (m, 1H), 4.05-4.11 (m, 2H), 3.76 (s, 3H), 3.51-3.57 (m, 2H), 2.98-3.14 (m, 2H), 2.26 (s, 3H)

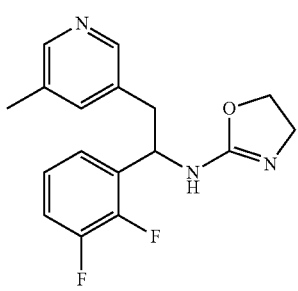

N-(1-(2,3-Difluorophenyl)-2-(5-methylpyridin-3-yl)ethyl)-4,5-dihydrooxazol-2-amine (Schemes G and F) $^1$H NMR (300 MHz, CD$_3$O CD$_3$): δ 8.25-8.26 (m, 1H), 8.20-8.21 (m, 1H), 7.43 (s, 1H), 7.30-7.36 (m, 1H), 7.14-7.21 (m, 2H), 5.19-5.24 (m, 1H), 4.08-4.14 (m, 2H), 3.48-3.56 (m, 2H), 2.99-3.16 (m, 2H), 2.26 (s, 3H)
Other Compounds of Interest are:

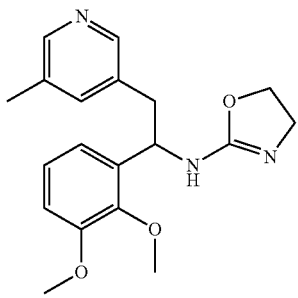 [SMILES: COc1cccc(C(Cc2cncc(C)c2)NC2=NCCO2)c1OC]

N-(1-(2,3-Dimethoxyphenyl)-2-(5-methylpyridin-3-yl)ethyl)-4,5-dihydrooxazol-2-amine

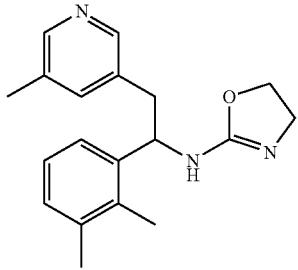 [SMILES: Cc1cncc(CC(NC2=NCCO2)c2cccc(C)c2C)c1]

48

N-(1-(2,3-Dimethylphenyl)-2-(5-methylpyridin-3-yl)ethyl)-4,5-dihydrooxazol-2-amine

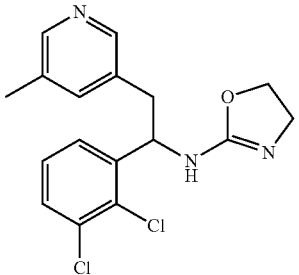 [SMILES: Cc1cncc(CC(NC2=NCCO2)c2cccc(Cl)c2Cl)c1]

N-(1-(2,3-Dichlorophenyl)-2-(5-methylpyridin-3-yl)ethyl)-4,5-dihydrooxazol-2-amine

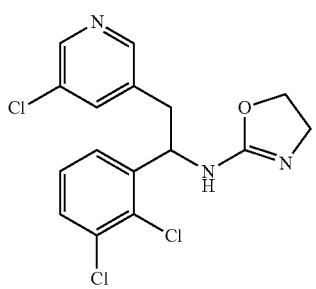 [SMILES: Clc1cncc(CC(NC2=NCCO2)c2cccc(Cl)c2Cl)c1]

N-(2-(5-Chloropyridin-3-yl)-(1-(2,3-dichlorophenyl)ethyl)-4,5-dihydrooxazol-2-amine

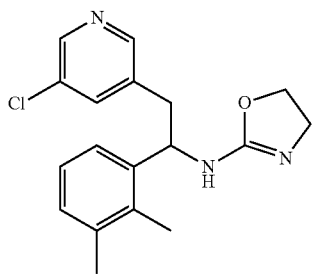 [SMILES: Cc1cccc(C(Cc2cncc(Cl)c2)NC2=NCCO2)c1C]

N-(2-(5-Chloropyridin-3-yl)-(1-(2,3-dimethylphenyl)ethyl)-4,5-dihydrooxazol-2-amine

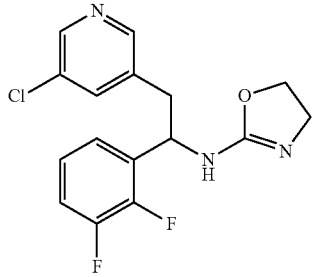 [SMILES: Fc1cccc(C(Cc2cncc(Cl)c2)NC2=NCCO2)c1F]

49

N-(2-(5-Chloropyridin-3-yl)-(1-(2,3-difluorophenyl)
ethyl)-4,5-dihydrooxazol-2-amine

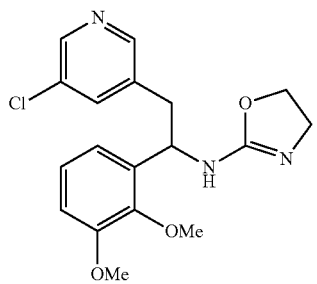 [SMILES: COc1cccc(C(Cc2cncc(Cl)c2)NC2=NCCO2)c1OC]

N-(2-(5-Chloropyridin-3-yl)-(1-(2,3-dimethoxyphe-
nyl)ethyl)-4,5-dihydrooxazol-2-amine

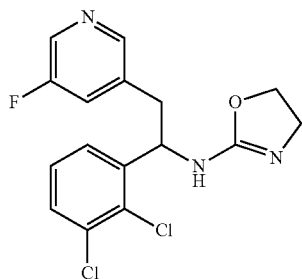 [SMILES: Fc1cncc(CC(NC2=NCCO2)c2cccc(Cl)c2Cl)c1]

N-(1-(2,3-Dichlorophenyl)-2-(5-fluoropyridin-3-yl)
ethyl)-4,5-dihydrooxazol-2-amine

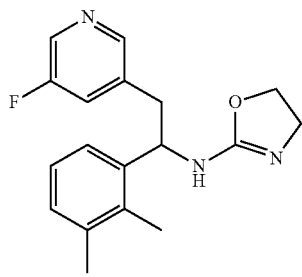 [SMILES: Cc1cccc(C(Cc2cncc(F)c2)NC2=NCCO2)c1C]

N-(1-(2,3-Dimethylphenyl)-2-(5-fluoropyridin-3-yl)
ethyl)-4,5-dihydrooxazol-2-amine

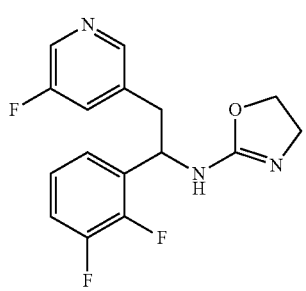 [SMILES: Fc1cncc(CC(NC2=NCCO2)c2cccc(F)c2F)c1]

50

N-(1-(2,3-Difluorophenyl)-2-(5-fluoropyridin-3-yl)
ethyl)-4,5-dihydrooxazol-2-amine

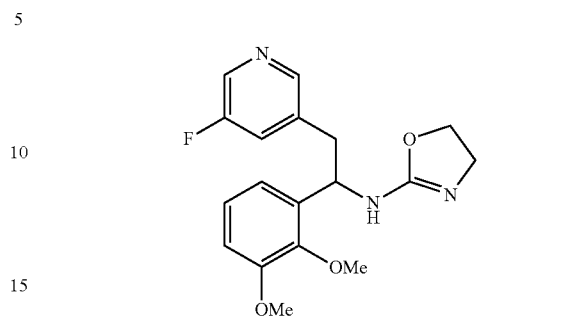

N-(1-(2,3-Dimethoxyphenyl)-2-(5-fluoropyridin-3-
yl)ethyl)-4,5-dihydrooxazol-2-amine

TABLE 2

| Biological Data: Intrinsic Activity | |
|---|---|
| Potency nM efficacy (EC50) | Alpha 2B |
| (structure) | 16 (0.74) |
| (structure) | 6.7 (0.93) |
| (structure) | 1.3 (1.05) |

TABLE 2-continued

| Structure | Biological Data: Potency nM (EC50) | Intrinsic Activity efficacy Alpha 2B |
|---|---|---|
| 2-chloropyridin-3-yl / 3-chlorophenyl oxazoline | 0.48 | (1.01) |
| 2-chloropyridin-3-yl / 3-methylphenyl oxazoline | 0.06 | (0.88) |
| 2-chloropyridin-3-yl / 3-fluorophenyl oxazoline | 0.09 | (0.87) |
| 2-chloropyridin-3-yl / 3-bromophenyl oxazoline | 0.14 | (1.01) |
| 2-fluoropyridin-3-yl / 3-chlorophenyl oxazoline | 0.21 | (0.81) |

TABLE 2-continued

| Structure | Biological Data: Potency nM (EC50) | Intrinsic Activity efficacy Alpha 2B |
|---|---|---|
| 6-chloropyridin-3-yl / 3-chlorophenyl oxazoline | 11 | (0.78) |
| 5-methylpyridin-3-yl / 3-chlorophenyl oxazoline | 4.0 | (1.12) |
| 5-methylpyridin-3-yl / 3-methylphenyl oxazoline | 3.0 | (1.1) |
| pyridin-3-yl / phenyl oxazoline | 4.5 | (0.76) |
| pyridin-3-yl / 3-methoxyphenyl oxazoline | 56 | (0.65) |

TABLE 2-continued

| Biological Data: Intrinsic Activity Potency nM efficacy (EC50) | Alpha 2B |
|---|---|
| [structure: 3-pyridyl-CH2-CH(NH-oxazoline)-2,3-dichlorophenyl] | 5.6 (0.89) |
| [structure: 3-pyridyl-CH2-CH(NH-oxazoline)-3-methylphenyl] | 8.2 (1.24) |
| [structure: 5-bromo-4-methyl-3-pyridyl-CH2-CH(NH-oxazoline)-3-chlorophenyl] | 1.9 (1.35) |
| [structure: 5-bromo-4-methyl-3-pyridyl-CH2-CH(NH-oxazoline)-3-methylphenyl] | 2.7 (1.02) |
| [structure: 5-methyl-4-methyl-3-pyridyl-CH2-CH(NH-oxazoline)-3-chlorophenyl] | 8.5 (0.9) |
| [structure: 4,5-dimethyl-3-pyridyl-CH2-CH(NH-oxazoline)-3-methylphenyl] | 3.9 (1.11) |
| [structure: 5-chloro-4-methyl-3-pyridyl-CH2-CH(NH-oxazoline)-3-chlorophenyl] | 5.6 (1.08) |

NA = Not Active

The Following Compounds are Preferred:

[1-(2,3-Dichloro-phenyl)-2-pyridin-3-yl-ethyl]-(4,5-dihydro-oxazol-2-yl)-amine (4,5-Dihydro-oxazol-2-yl)-[1-(2,3-dimethyl-phenyl)-2-pyridin-4-yl-ethyl]-amine (4,5-Dihydro-oxazol-2-yl)-[1-(2,3-dimethyl-phenyl)-2-pyridin-3-yl-ethyl]-amine N-[1-(2,3-dimethylphenyl)-2-pyridin-3-ylethyl]-4,5-dihydro-1,3-thiazol-2-amine N-[1-(2,3-dimethylphenyl)-2-pyridin-3-ylethyl]-4,5-dihydro-1,3-oxazol-2-amine 1-(3-chloro-2-fluorophenyl)-N-imidazolidin-2-ylidene-2-pyridin-4-ylethanamine

[1-(2,3-Dichloro-phenyl)-2-pyridin-4-yl-ethyl]-imidazolidin-2-ylidene-amine

N-[1-(3-fluorophenyl)-2-pyridin-4-ylethyl]-4,5-dihydro-1,3-oxazol-2-amine 1-(2,3-dimethylphenyl)-N-imidazolidin-2-ylidene-2-pyridin-4-ylethanamine (1-Phenyl-2-pyridin-4-yl-ethyl)thiazolidin-(2Z)-ylidene-amine

[1-(3-Chloro-phenyl)-2-(5-methyl-pyridin-3-yl)-ethyl]-(4,5-dihydro-oxazol-2-yl)-amine (4,5-Dihydro-oxazol-2-yl)-[2-(5-methyl-pyridin-3-yl)-1-m-tolyl-ethyl]-amine (4,5-Dihydro-oxazol-2-yl)-(1-phenyl-2-pyridin-3-yl-ethyl)amine (4,5-Dihydro-oxazol-2-yl)-[1-(2,3-dimethyl-phenyl)-2-pyridin-2-yl-ethyl]-amine Part II: Syntheses of Aminooxazolines, Aminothiazolines, and Aminoimidazolines Aminooxazoline

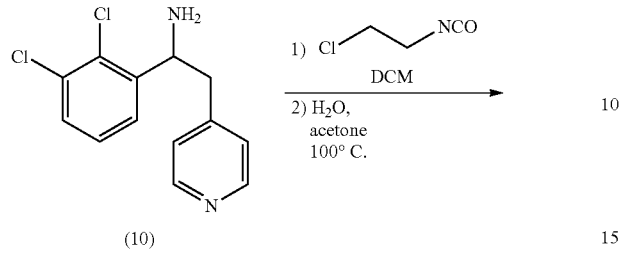

(10)

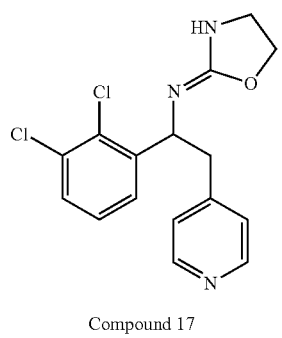

Compound 17

1-(2,3-Dichlorophenyl)-N-(oxazolidin-2-ylidene)-2-(pyridin-4-yl)ethanamine Compound 17: 1-(2,3-dichlorophenyl)-2-(pyridin-4-yl)ethanamine (0.30 g, 1.13 mmol) in dichloromethane (6.0 mL) was added chloroethylisocyanate (0.11 mL, 1.29 mol). The solution was stirred at room temperature for one hour. The solvent was removed under vacuum. The residue was added water, acetone, and heated at 100° C. for one hour. The mixture was cooled to room temperature, and basified with NaOH (2M) to pH>7. The aqueous layer was extracted with chloroform/isopropanol (3:1, 3×, 200 mL). The pooled organic layer was dried over magnesium sulfate. The mixture was filtered. The filtrate was added silica gel, and the solvents were removed under vacuum. Purification by chromatography on silica gel (2% saturated ammonia methanol in dichloromethane) gave 1-(2,3-dichlorophenyl)-N-(oxazolidin-2-ylidene)-2-(pyridin-4-yl)ethanamine Compound 17 as a white solid (0.21 g, 0.63 mmol, 56% yield).

Compound 17 $^1$H NMR (300 MHz, CD$_3$OD): δ=8.44-8.42 (m, 2H), 7.46-7.31 (m, 5H), 5.28 (dd, J=10.2, 4.2 Hz, 1H), 4.18 (t, J=8.7 Hz, 2H), 3.52 (t, J=8.4 Hz, 2H), 3.16 (dd, J=13.8, 3.6 Hz, 1H), 2.87 (dd, J=13.8, 10.5 Hz, 1H).

Aminothiazoline:

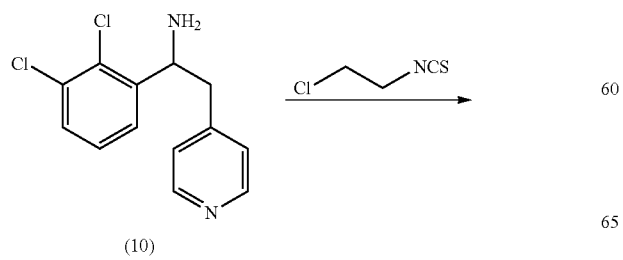

(10)

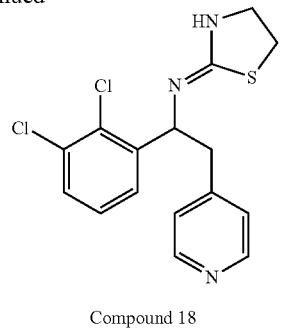

Compound 18

1-(2,3-Dichlorophenyl)-2-(pyridin-4-yl)-N-(thiazolidin-2-ylidene)ethanamine Compound 18: 1-(2,3-dichlorophenyl)-2-(pyridin-4-yl)ethanamine (0.30 g, 1.13 mmol) in dichloromethane (6 mL) was added chloroethylisothiocyanate (0.097 mL, 0.988 mmol). The solution was stirred at room temperature for 1.5 hour, and quenched with water. The aqueous layer was extracted with dichloromethane (3×). The pooled organic layer was dried over magnesium sulfate. The mixture was filtered. The filtrate was added silica gel, and the solvents were removed under vacuum. Purification by chromatography on silica gel (2 to 10% methanol in dichloromethane) gave a crude material, which was recrystallized in methanol/water to give 1-(2,3-dichlorophenyl)-2-(pyridin-4-yl)-N-(thiazolidin-2-ylidene)ethanamine Compound 18 as a solid (15.9 mg, 0.045 mmol, 4% yield).

1-(2,3-dichlorophenyl)-2-(pyridin-4-yl)-N-(thiazolidin-2-ylidene)ethanamine Compound 18 $^1$H NMR (300 MHz, CDCl$_3$): δ=8.50-8.48 (m, 2H), 7.39 (dd, J=7.5, 2.1 Hz, 1H), 7.24-7.14 (m, 2H), 7.10-7.08 (m, 2H), 5.27 (dd, J=8.4, 4.8 Hz, 1H), 3.77 (t, J=6.9 Hz, 2H), 3.22 (t, J=7.2 Hz, 2H), 3.22-3.15 (m, 1H), 2.94 (dd, J=13.8, 8.1 Hz, 1H).

Aminoimidazoline

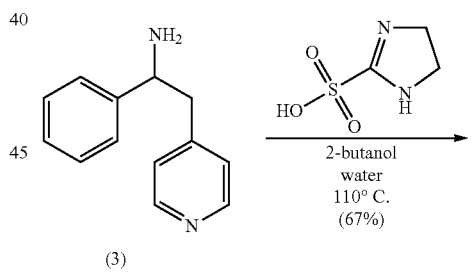

(3)

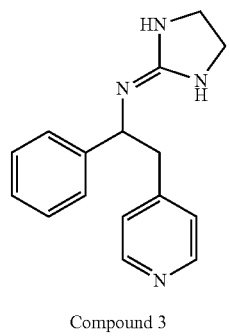

Compound 3

N-(Imidazolidin-2-ylidene)-1-phenyl-2-(pyridin-4-yl)ethanamine Compound 3: A mixture of 1-phenyl-2-(pyridin-4-yl)ethanamine (0.23 g, 1.18 mmol), and 4,5-dihydro-1H-imidazole-2-sulfonic acid (0.18 g, 1.16 mmol) in 2-butanol (5 mL), water (1 mL) were heated at 110° C. for 3 hours. The solution was cooled to room temperature. The solvents were removed under vacuum. The residue was dissolved in methanol, and added amino modified silica gel. The solvent was removed under vacuum. Purification by chromatography on amino modified silica gel (100% ethyl acetate to 7% methanol in dichloromethane) gave N-(imidazolidin-2-ylidene)-1-phenyl-2-(pyridin-4-yl)ethanamine Compound 3 as a while solid (0.21 g, 0.80 mmol, 67% yield).

Compound 3: $^1$H NMR (300 MHz, CD$_3$OD): δ=8.40-8.38 (m, 2H), 7.35-7.34 (m, 5H), 7.31-7.29 (m, 2H), 4.80 (dd, J=8.4, 6.8 Hz, 1H), 3.51 (s, 4H), 3.17 (dd, J=8.4, 5.4 Hz, 2H).

NOTE: The chiral amines were obtained as the dihydrochloride salt from Netchem Inc. They were dissolved in water. The aqueous layer was basified with NaOH (2M) to pH>7. The aqueous layer was extracted with dichloromethane. The pooled organic layers were worked-up in the standard fashion. R—N-(imidazolidin-2-ylidene)-1-phenyl-2-(pyridin-4-yl)ethanamine Compound 29: $[α]_D^{20}$=+13.4 (c 1.26, CHCl$_3$) and S—N-(imidazolidin-2-ylidene)-1-phenyl-2-(pyridin-4-yl)ethanamine Compound 29-1: $[α]_D^{20}$=−23.1 (c 1.35, 83% CHCl$_3$, 17% MeOH).

The following compounds were synthesized by one of the general methods described above, and for preparation of the amine precursor refer to Schemes A-F.

1-(2,3-Dichlorophenyl)-N-(imidazolidin-2-ylidene)-2-(pyridin-4-yl)ethanamine, Compound 32: (Scheme C) $^1$H NMR (300 MHz, CD$_3$OD): δ=8.41-8.39 (m, 2H), 7.45 (dd, J=3.6, 1.5 Hz, 1H), 7.43 (dd, J=3.9, 1.5 Hz, 1H), 7.36-7.34 (m, 2H), 7.29 (t, J=7.8 Hz, 1H), 5.19 (dd, J=9.6, 4.5 Hz, 1H), 3.35-3.34 (m, 4H), 3.17 (dd, J=14.1, 4.2 Hz, 1H), 2.88 (dd, J=14.1, 9.6 Hz, 1H).

1-(3-Chlorophenyl)-N-(oxazolidin-2-ylidene)-2-(pyridin-4-yl)ethanamine, Compound 8: (Scheme B) $^1$H NMR (300 MHz, CDCl$_3$): δ=8.47-8.45 (m, 2H), 7.28-7.23 (m, 3H), 7.11-7.08 (m, 1H), 7.03-7.01 (m, 2H), 4.90 (t, J=7.2 Hz, 1H), 4.19 (td, J=8.7, 2.4 Hz, 2H), 3.67 (t, J=8.4 Hz, 2H), 3.12-2.98 (m, 2H)

N-(Oxazolidin-2-ylidene)-1-phenyl-2-(pyridin-4-yl)ethanamine, Compound 1 (Scheme A) $^1$H NMR (300 MHz, CDCl$_3$): δ=8.44-8.42 (m, 2H), 7.33-7.26 (m, 3H), 7.21-7.18 (m, 2H), 6.99-6.97 (m, 2H), 4.93 (t, J=6.9 Hz, 1H), 4.23-4.16 (m, 2H), 3.71 (t, J=8.4 Hz, 2H), 3.20-3.02 (m, 2H).

Enantiomers, R—N-(oxazolidin-2-ylidene)-1-phenyl-2-(pyridin-4-yl)ethanamine Compound 30: [α]=−12.9 (c 1.34, CHCl$_3$) and S—N-(oxazolidin-2-ylidene)-1-phenyl-2-(pyridin-4-yl)ethanamine Compound 30-1: $[α]_D^{20}$=+4.06 (c 0.842, CHCl$_3$), were prepared.

1-Phenyl-2-(pyridin-4-yl)-N-(thiazolidin-2-ylidene)ethanamine, Compound 2 (Scheme A) $^1$H NMR (300 MHz, CDCl$_3$): δ=8.42 (d, J=5.7 Hz, 2H), 7.32-7.25 (m, 3H), 7.22-7.19 (m, 2H), 6.98 (d, J=6.0 Hz, 2H), 4.91 (t, J=6.6 Hz, 1H), 3.87 (t, J=7.2 Hz, 2H), 3.28-7.17 (m, 3H), 3.10-3.04 (m, 1H). Enantiomers, R-1-phenyl-2-(pyridin-4-yl)-N-(thiazolidin-2-ylidene)ethanamine Compound 31: [α]v=−3.56 (c 1.22, CHCl$_3$) and S-1-phenyl-2-(pyridin-4-yl)-N-(thiazolidin-2-ylidene)ethanamine Compound 31-1 (95% pure): $[α]_D^{20}$=+15.6 (c 0.925, CHCl$_3$) were prepared.

N-(Imidazolidin-2-ylidene)-1-phenyl-2-(pyrazin-2-yl) ethanamine, Compound 15: (Scheme A) $^1$H NMR (300 MHz, CD$_3$OD): δ=8.60 (dd, J=1.5, 2.4 Hz, 1H), 8.45 (d, J=2.7 Hz, 1H), 8.40 (d, J=1.5 Hz, 1H), 7.36-7.29 (m, 5H), 5.10 (dd, J=6, 8.4 Hz, 1H), 3.58 (s, 4H), 3.36 (dd, J=5.1, 8.1 Hz, 2H).

N-(Oxazolidin-2-ylidene)-1-phenyl-2-(pyrazin-2-yl)ethanamine, Compound 14: (Scheme A) $^1$H NMR (300 MHz, CD$_3$OD): δ=8.49 (dd, J=1.2, 2.4 Hz, 1H), 8.39 (d, J=2.4 Hz, 1H), 8.22 (d, J=1.5 Hz, 1H), 7.27-7.20 (m, 5H), 5.12 (t, J=6.3 Hz, 1H), 4.22 (t, J=8.7 Hz, 2H), 3.70 (t, J=8.7 Hz, 2H), 3.29 (d, J=6.3 Hz, 2H).

1-Phenyl-2-(pyrazin-2-yl)-N-(thiazolidin-2-ylidene)ethanamine, Compound 16: (Scheme A) $^1$H NMR (300 MHz, CD$_3$OD): δ=8.60 (dd, J=1.5, 2.7 Hz, 1H), 8.46 (d, J=2.1 Hz, 1H), 8.43 (d, J=1.5 Hz, 1H), 7.37-7.27 (m, 5H), 5.30 (dd, J=1.8, 7.8 Hz, 1H), 3.86 (t, J=7.2 Hz, 2H), 3.58-3.33 (m, 2H), 3.29 (d, J=6.3 Hz, 2H).

1-(2,3-Dimethylphenyl)-2-(pyridin-4-yl)-N-(thiazolidin-2-ylidene)ethanamine, Compound 4: (Scheme C) $^1$H NMR (300 MHz, CD$_3$OD): δ=8.34-8.32 (m, 2H), 7.43-7.40 (m, 1H), 7.25-7.23 (m, 2H), 7.05-7.00 (m, 2H), 4.62 (dd, J=3, 9 Hz, 1H), 4.05-3.88 (m, 2H), 3.09 (t, J=6 Hz, 2H), 3.05-3.00 (m, 2H), 2.26 (s, 6H).

1-(2,3-Dimethylphenyl)-N-(oxazolidin-2-ylidene)-2-(pyridin-4-yl)ethanamine, Compound 6: (Scheme C) $^1$H NMR (300 MHz, CD$_3$OD): δ=8.38-8.36 (m, 2H), 7.30-7.28 (m, 2H), 7.25-7.22 (m, 1H), 7.10-7.04 (m, 2H), 5.15 (dd, J=6.3, 9 Hz, 1H), 4.17 (t, J=8.4 Hz, 2H), 3.55 (t, J=8.4 Hz, 2H), 3.01-2.97 (m, 2H), 2.25 (s, 3H), 2.22 (s, 3H).

1-(2,3-Dimethylphenyl)-N-(imidazolidin-2-ylidene)-2-(pyridin-4-yl)ethanamine, Compound 5: (Scheme C) $^1$H NMR (300 MHz, CD$_3$OD): δ=8.44 (d, J=5.7 Hz, 2H), 7.35 (d, J=6.3 Hz, 2H), 7.24-7.21 (m, 1H), 7.17-7.13 (m, 2H), 5.09 (dd, J=5.4, 9 Hz, 1H), 3.58 (s, 4H), 3.15 (ddd, J=5.4, 14.4, 27.3 Hz, 2H), 2.29 (s, 3H), 2.26 (s, 3H).

1-(3-Fluorophenyl)-2-(pyridin-4-yl)-N-(thiazolidin-2-ylidene)ethanamine, Compound 23:
(Scheme E) $^1$H NMR (300 MHz, CD$_3$OD): δ=8.45-8.43 (m, 2H), 7.45-7.38 (m, 1H), 7.32-7.30 (m, 2H), 7.18-7.06 (m, 3H), 5.00 (t, J=6.9 Hz, 1H), 3.94-3.82 (m, 2H), 3.51 (t, J=7.8 Hz, 2H), 3.25 (d, J=7.8 Hz, 2H).

1-(3-Fluorophenyl)-N-(oxazolidin-2-ylidene)-2-(pyridin-4-yl)ethanamine, Compound 24: (Scheme E) $^1$H NMR (300 MHz, CD$_3$OD): δ=8.39-8.37 (m, 2H), 7.34-7.27 (m, 3H), 7.15-7.07 (m, 2H), 6.99-6.93 (m, 1H), 4.84 (t, J=7.5 Hz, 1H), 4.20 (t, J=8.1 Hz, 2H), 3.58 (t, J=8.1 Hz, 2H), 3.25 (d, J=7.5 Hz, 2H).

1-(3-Fluorophenyl)-N-(imidazolidin-2-ylidene)-2-(pyridin-4-yl)ethanamine, Compound 25: (Scheme E) $^1$H NMR (300 MHz, CD$_3$OD): δ=8.45-8.43 (m, 2H), 7.43-7.36 (m, 1H), 7.30-7.28 (m, 2H), 7.16-7.04 (m, 2H), 4.84 (t, J=7.5 Hz, 1H), 3.60 (s, 4H), 3.20 (dd, J=1.2, 6.3 Hz, 2H).

1-(3-Chloro-2-fluorophenyl)-N-(imidazolidin-2-ylidene)-2-(pyridin-4-yl)ethanamine, Compound 20: (Scheme C) $^1$H NMR (300 MHz, CD$_3$OD): δ=8.43-8.41 (m, 2H), 7.44-7.37 (m, 2H), 7.34-7.32 (m, 2H), 7.20-7.17 (m, 1H), 5.09 (t, J=7.2 Hz, 1H), 3.50 (s, 4H), 3.19 (d, J=7.2 Hz, 2H).

1-(3-Chloro-2-fluorophenyl)-N-(oxazolidin-2-ylidene)-2-(pyridin-4-yl)ethanamine, Compound 19: (Scheme C) $^1$H NMR (300 MHz, CD$_3$OD): δ=8.41-8.39 (m, 2H), 7.39-7.29 (m, 4H), 7.16-7.10 (m, 1H), 5.14 (t, J=7.8 Hz, 1H), 4.19 (t, J=8.7 Hz, 2H), 3.54 (t, J=8.7 Hz, 2H), 3.08-3.05 (m, 2H).

1-(2,3-Dimethylphenyl)-N-(oxazolidin-2-ylidene)-2-(pyridin-3-yl)ethanamine, Compound 21: (Scheme D) $^1$H NMR (300 MHz, CD$_3$OD): δ=8.35-8.33 (m, 2H), 7.70-7.68 (m, 1H), 7.32 (dd, J=4.8, 7.8 Hz, 1H), 7.24 (d, J=7.5 Hz, 1H), 7.23-7.02 (m, 2H), 5.08 (t, J=7.5 Hz, 1H), 4.17 (t, J=8.4 Hz, 2H), 3.55 (t, J=8.4 Hz, 2H), 2.98 (d, J=, 7.2 Hz, 2H), (2.24 (s, 3H). 2.18 (s, 3H).

1-(2,3-Dimethylphenyl)-2-(pyridin-3-yl)-N-(thiazolidin-2-ylidene)ethanamine, Compound 22: (Scheme D) $^1$H NMR (300 MHz, CD$_3$OD): δ=8.38-8.33 (m, 2H), 7.70 (d, J=7.8 Hz, 1H), 7.33 (dd, J=5.1, 7.8 Hz, 1H), 7.23-7.21 (m, 1H), 7.14-

7.09 (m, 2H), 5.20 (t, J=7.5 Hz, 1H), 3.82-3.76 (m, 2H), 3.33 (t, J=8.1 Hz, 2H), 3.10 (d, J=7.5 Hz, 2H), (2.25 (s, 3H). 2.16 (s, 3H).

1-(2-Chlorophenyl)-N-(oxazolidin-2-ylidene)-2-(pyridin-4-yl)ethanamine, Compound 26 (Scheme F) $^1$H NMR (300 MHz, CDCl$_3$): δ 8.46-8.48 (m, 2H), 7.35-7.39 (m, 1H), 7.20-7.25 (m, 3H), 7.08-7.10 (m, 2H), 5.30-5.34 (m, 1H), 4.14-4.20 (m, 2H), 3.63-3.69 (m, 2H), 3.16-3.22 (m, 1H), 2.91-2.99 (m, 1H).

1-(2-Chlorophenyl)-2-(pyridin-4-yl)-N-(thiazolidin-2-ylidene)ethanamine, Compound 27 (Scheme F) $^1$H NMR (300 MHz, CDCl$_3$): δ 8.46-8.48 (m, 2H), 7.35-7.38 (m, 1H), 7.20-7.29 (m, 3H), 7.06-7.08 (m, 2H), 5.25-5.29 (m, 1H), 3.78-3.84 (m, 2H), 3.16-3.25 (m, 3H), 2.96-3.04 (m, 1H).

1-(2-Chlorophenyl)-N-(imidazolidin-2-ylidene)-2-(pyridin-4-yl)ethanamine, Compound 28 (Scheme F) $^1$H NMR (300 MHz, CDCl$_3$): δ 8.49-8.50 (m, 2H), 7.70-7.73 (m, 1H), 7.27-7.42 (m, 5H), 4.98 (br, 1H), 3.61 (br, 4H), 3.07-3.24 (m, 2H).

1-(2,3-Dimethylphenyl)-N-(oxazolidin-2-ylidene)-2-(pyridin-4-yl)ethanamine, Compound 9 (Schemes B and F) $^1$H NMR (300 MHz, CD$_3$OD): δ 8.36-8.38 (m, 2H), 7.21-7.29 (m, 4H), 6.88-6.98 (m, 2H), 5.11-5.16 (m, 1H), 4.23-4.29 (m, 2H), 3.86 (s, 3H), 3.56-3.62 (m, 2H), 3.12-3.18 (m, 1H), 2.93-3.01 (m, 1H).

1-(2-Methoxyphenyl)-2-(pyridin-4-yl)-N-(thiazolidin-2-ylidene)ethanamine, Compound 7 (Schemes B and F) $^1$H NMR (300 MHz, CD$_3$OD): δ 8.35-8.37 (m, 2H), 7.21-7.28 (m, 4H), 6.87-6.97 (m, 2H), 5.27-5.32 (m, 1H), 3.85 (s, 1H), 3.72-3.77 (m, 2H), 3.10-3.21 (m, 3H), 2.90-2.97 (m, 1H).

N-(Imidazolidin-2-ylidene)-1-(2-methoxyphenyl)-2-(pyridin-4-yl)ethanamine, Compound 10 (Schemes B and F) $^1$H NMR (300 MHz, CD$_3$OD): δ 8.40-8.42 (m, 2H), 7.28-7.33 (m, 4H), 6.93-7.04 (m, 2H), 5.00-5.05 (m, 1H), 3.89 (s, 1H), 3.56 (s, 4H), 3.22-3.29 (m, 1H), 3.07-3.14 (m, 1H).

1-(2-Methoxyphenyl)-N-(oxazolidin-2-ylidene)-2-(pyridin-3-yl)ethanamine, Compound 13 (Schemes B and F) $^1$H NMR (300 MHz, CD$_3$OD): δ 8.30-8.33 (m, 2H), 7.65-7.69 (m, 1H), 7.19-7.31 (m, 3H), 6.86-6.95 (m, 2H), 5.06-5.11 (m, 1H), 4.11-4.17 (m, 2H), 3.82 (s, 3H), 3.50-3.56 (m, 2H), 3.05-3.12 (m, 1H), 2.89-2.97 (m, 1H).

1-(2-Methoxyphenyl)-2-(pyridin-3-yl)-N-(thiazolidin-2-ylidene)ethanamine, Compound 11 (Schemes B and F) $^1$H NMR (300 MHz, CD$_3$OD): δ 8.33-8.35 (m, 2H), 7.67-7.69 (m, 1H), 7.21-7.34 (m, 3H), 6.88-6.97 (m, 2H), 5.20-5.24 (m, 1H), 3.84 (s, 3H), 3.73-3.78 (m, 2H), 3.20-3.25 (m, 2H), 3.11-3.17 (m, 1H), 3.02-2.94 (m, 1H).

N-(Imidazolidin-2-ylidene)-1-(2-methoxyphenyl)-2-(pyridin-3-yl)ethanamine, Compound 12 (Schemes B and F) $^1$H NMR (300 MHz, CD$_3$OD): δ 8.37-8.39 (m, 2H), 7.71-7.74 (m, 1H), 7.25-7.37 (m, 3H), 6.92-7.03 (m, 2H), 4.94-4.98 (m, 1H), 3.88 (s, 3H), 3.57 (s, 4H), 3.10-3.27 (m, 2H).

Alleviation of Chronic Pain

A model in accordance with Kim and Chung 1992, Pain 150, pp 355-363 (Chung model), for chronic pain (in particular peripheral neuropathy) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, typically six rats per test group are administered the test drugs by intraperitoneal (i.p.) injection or oral gavage. For i.p. injection, the compounds are formulated in approximately 10 to 50% DMSO and given in a volume of 1 ml/kg body weight.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980). The post-drug threshold is compared to the pre-drug threshold and the percent reversal of tactile sensitivity is calculated based on a normal threshold of 15.1 grams. The results are expressed in percent (%) MPE, where the MPE value reflects the percentage reversal of pain threshold to that of a normal animal (100%).

TABLE 3

Activity of the Compounds of the Invention in the Chung Model of Neuropathic Pain
(% Pain Reversal ± SEM)
Dose via i.p. route of administration of Compound 21

| Dose i.p. | 30 min | 60 min |
|---|---|---|
| 0.10 mg | 27 ± 5% | ~10 |
| 0.30 mg | 60.1 ± 12.8% | 21.5 ± 6.1% |
| 1.0 mg | 95.9 ± 4.1% | 77.0 ± 7.6% |

Dose and Route of Administration of Compound 21

The results shown in Table 3 (also set forth graphically in FIG. 1) illustrate that these compounds of the invention significantly alleviate allodynic pain, and based on these test and/or on the compounds ability to activate alpha$_{2B}$ and/or alpha$_{2C}$ adrenergic receptors in preference over alpha$_{2A}$ adrenergic receptors, the compounds of the invention are expected to be useful as analgesics to alleviate allodynia and chronic pain.

While this invention has been described with respect to these specific examples, it is understood that other modifications and variations are possible without departing from the spirit of the invention.

What is claimed is:

1. A compound having the structure:

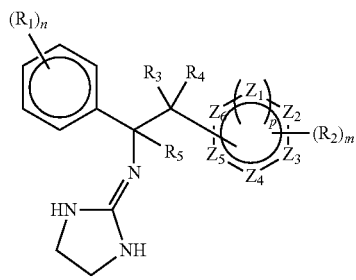

wherein:
- $Z_1$-$Z_6$ are each independently CH, N with the proviso that one of $Z_1$-$Z_6$ is N;
- n and m are each independently 1 to 5;
- p is 1;
- each $R_1$ and $R_2$ is independently H, lower alkyl, halo, hydroxy, alkoxy, trifluoromethyl, —N($R_6$)$_2$, —CN, —CO$_2$$R_6$, or —CH$_2$OH;
- $R_3$, $R_4$, $R_5$, and $R_6$ are each independently H;

or a pharmaceutically acceptable salt, thereof.

2. The compound of claim 1, wherein $R_1$ is H, lower alkyl, chloro, fluoro, trifluoromethyl, or methoxy.

3. A compound having the structure

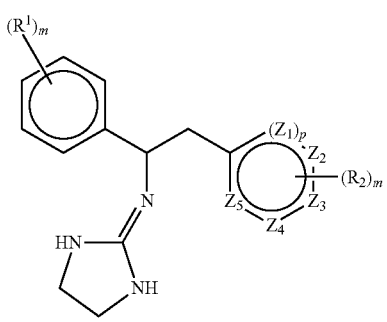

wherein:
- $Z_1$-$Z_5$ are each independently CH, N, with the proviso that one of $Z_1$-$Z_5$ is N;
- n and m are each independently 1 to 5;
- p is 1;
- each $R_1$ and $R_2$ is independently H, lower alkyl, halo, hydroxy, alkoxy, or trifluoromethyl;

or a pharmaceutically acceptable salts salt thereof.

4. The compound of claim 3 having the structure:

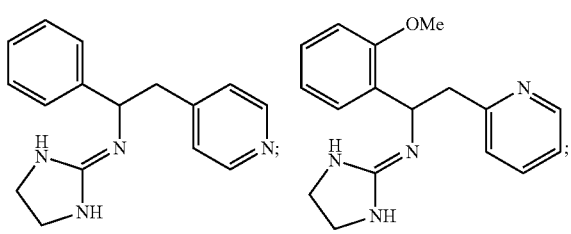

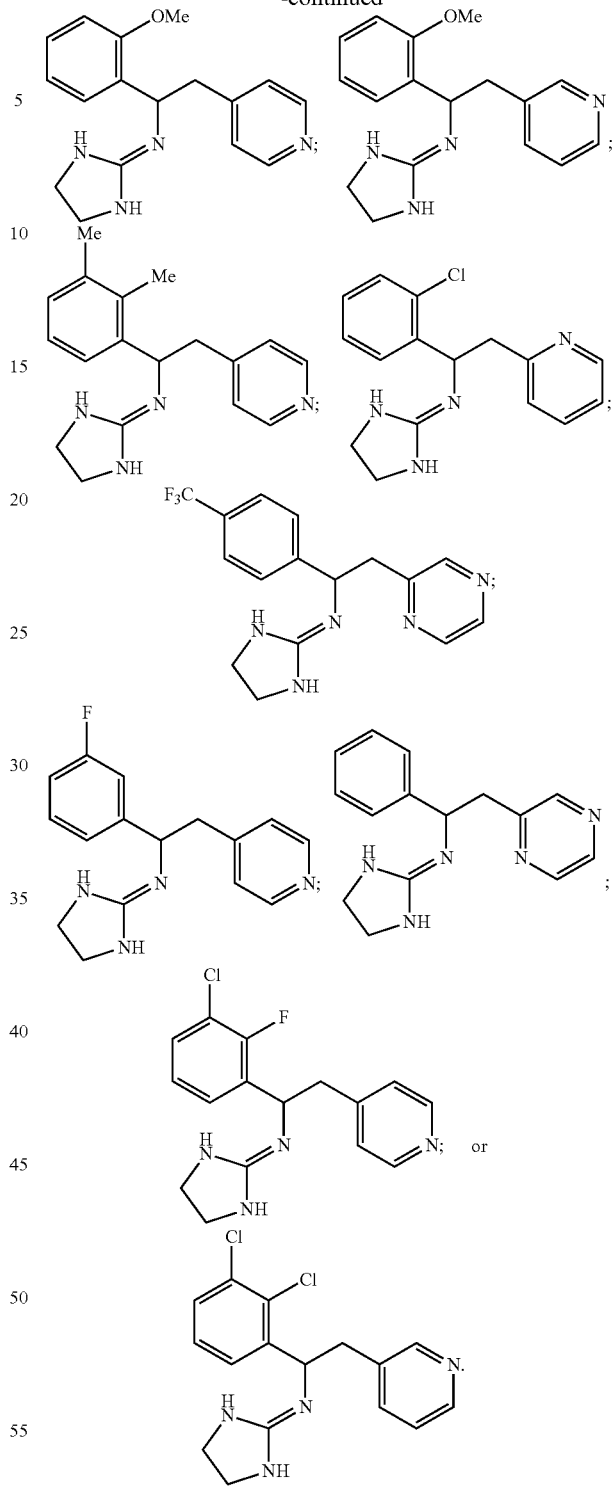

5. A pharmaceutical composition comprising at least one compound of claim 1 and a pharmaceutically acceptable carrier.

6. A pharmaceutical composition comprising at least one compound of claim 1, or any combination thereof, or a pharmaceutically acceptable salt, thereof and a pharmaceutically acceptable carrier.

* * * * *

UNITED STATES PATENT AND TRADEMARK OFFICE
CERTIFICATE OF CORRECTION

PATENT NO. : 8,362,022 B2
APPLICATION NO. : 12/811773
DATED : January 29, 2013
INVENTOR(S) : Todd M. Heidelbaugh et al.

It is certified that error appears in the above-identified patent and that said Letters Patent is hereby corrected as shown below:

In the Specifications:

In column 1, lines 6-8, delete "This application claims the benefit of U.S. Provisional Application Ser. No. 61/022,158, filed Jan. 18, 2008, which is hereby incorporated by reference in its entirety." and insert -- This is a national stage application under 35 U.S.C. § 371 of PCT patent application PCT/US2009/30886, filed on January 14, 2009, which claims the benefit of U.S. Provisional Patent Application 61/022,158, filed January 18, 2008, each of which is hereby incorporated by reference in its entirety. --, therefor.

In column 4, line 4, before "—S—," delete "—C(O)—,".

In column 13, lines 5-9, delete " 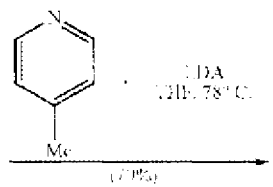 " and insert -- 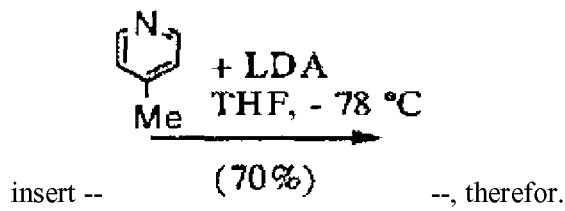 --, therefor.

In column 13, lines 35-39, delete " 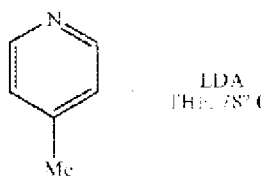 " and

Signed and Sealed this
Seventh Day of May, 2013

Teresa Stanek Rea
*Acting Director of the United States Patent and Trademark Office* insert -- 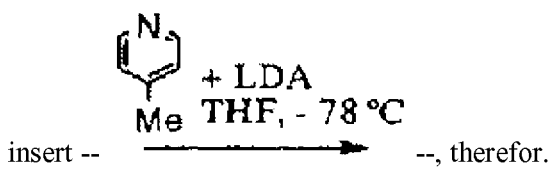 --, therefor.

In column 14, lines 32-40, delete " 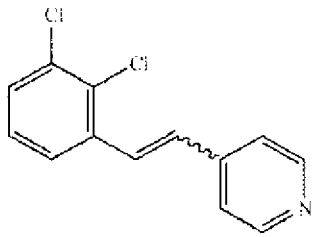 " and insert -- 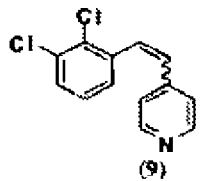 --, therefor.

In column 19, lines 40-45, delete " 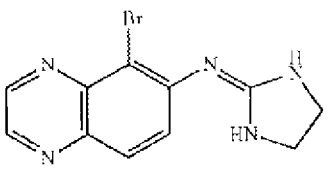 " and insert -- 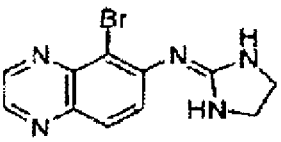 --, therefor.

In column 20, line 37, delete "(A β and A fibers)" and insert -- (Aβ and A* fibers) --, therefor.

In column 20, line 46, delete "A β" and insert -- Aβ --, therefor.

In column 21, line 14, delete "VASUCLAR" and insert -- VASCULAR --, therefor.

In column 21, line 37, delete "(PONS)," and insert -- (POHS), --, therefor.

In column 28, line 41, delete "erythematosis" and insert -- erythematosus --, therefor.

In column 28, line 43, delete "(hyperhydrosis)" and insert -- (hyperhidrosis) --, therefor.

In column 29, line 43, delete "chromic" and insert -- chronic --, therefor.

In column 31, line 21, delete "and or" and insert -- and/or --, therefor.

In column 32, lines 46-55, delete " 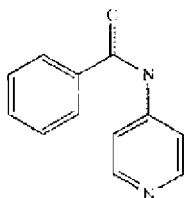 " and insert -- 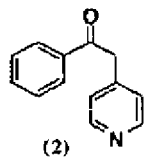 --, therefor.

In column 34, line 31-39, delete " 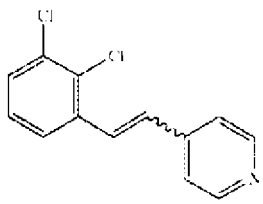 " and insert -- 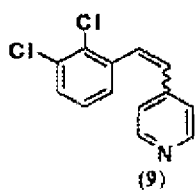 --, therefor.

In column 37, line 39, delete "(21)" and insert -- (21): --, therefor.

In column 37, line 64, delete "(23)" and insert -- (23): --, therefor.

In column 38, line 17, delete "(1.2 g 76%)" and insert -- (1.2 g, 76%) --, therefor.

In column 43, line 41, delete "(s 1H)," and insert -- (s, 1H), --, therefor.

In column 46, line 17, after "amine" delete "amine".

In column 47, line 16, delete "CD$_3$O CD$_3$):" and insert -- CD$_3$OCD$_3$): --, therefor.

In column 47, line 33, delete "CD$_3$O CD$_3$):" and insert -- CD$_3$OCD$_3$): --, therefor.

In column 57, line 39, after "2H)" insert -- . --.

In column 58, line 66, delete "6=" and insert -- δ= --, therefor.

In column 59, line 2, delete "(2.25 (s, 3H). 2.16" and insert -- 2.25 (s, 3H), 2.16 --, therefor.

In column 60, line 6, delete "Novacaine." and insert -- Novocaine. --, therefor.

CERTIFICATE OF CORRECTION (continued)
U.S. Pat. No. 8,362,022 B2

In the Claims:

In column 61, lines 32-44, in claim 3, delete " 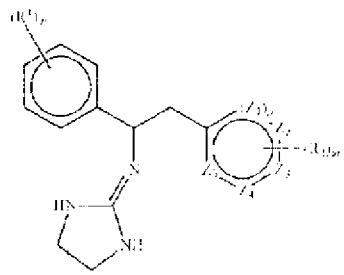 " and insert -- 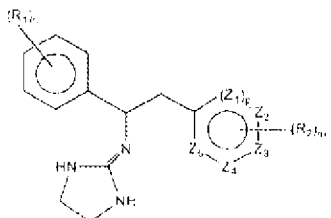 --, therefor.

In column 61, line 54, in claim 3, before "salt" delete "salts".